United States Patent
Cater et al.

(10) Patent No.: US 12,209,277 B2
(45) Date of Patent: Jan. 28, 2025

(54) METHODS AND COMPOSITIONS FOR DECONVOLUTING PARTITION BARCODES

(71) Applicant: Bio-Rad Laboratories, Inc., Hercules, CA (US)

(72) Inventors: Sean Cater, Pinole, CA (US); Lucas Frenz, San Leandro, CA (US); Andrew Kohlway, Pleasanton, CA (US); Jennifer Chew, Sunnyvale, CA (US); Rob Ray, Oakland, CA (US); Ronald Lebofsky, Kensington, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 326 days.

(21) Appl. No.: 16/260,475

(22) Filed: Jan. 29, 2019

(65) Prior Publication Data
US 2019/0241944 A1   Aug. 8, 2019

Related U.S. Application Data

(60) Provisional application No. 62/624,400, filed on Jan. 31, 2018.

(51) Int. Cl.
*C12Q 1/6853* (2018.01)
*C12N 15/10* (2006.01)
*C12Q 1/6806* (2018.01)

(52) U.S. Cl.
CPC ....... *C12Q 1/6853* (2013.01); *C12N 15/1065* (2013.01); *C12Q 1/6806* (2013.01)

(58) Field of Classification Search
CPC . C12Q 1/6853; C12Q 1/6806; C12N 15/1065
See application file for complete search history.

(56) References Cited

U.S. PATENT DOCUMENTS

| | | | |
|---|---|---|---|
| 10,730,030 B2 * | 8/2020 | Lebofsky et al. | ... B01J 19/0046 |
| 2006/0281079 A1 | 12/2006 | Eickbush et al. | |
| 2009/0035777 A1 * | 2/2009 | Kokoris et al. | ................... 435/6 |
| 2012/0034603 A1 | 2/2012 | Oliphant et al. | |
| 2016/0312276 A1 | 10/2016 | Fu et al. | |
| 2017/0232417 A1 | 8/2017 | Lebofsky et al. | |
| 2020/0324264 A1 | 10/2020 | Lebofsky et al. | |

FOREIGN PATENT DOCUMENTS

| | | | |
|---|---|---|---|
| WO | WO 2011/056866 A2 * | 5/2011 | |
| WO | WO-2014144495 A1 * | 9/2014 | ............. C07K 16/00 |
| WO | 2015/200541 A1 | 12/2015 | |
| WO | 2017/079593 A1 | 5/2017 | |
| WO | 2017/120531 A1 | 7/2017 | |
| WO | 2018/017914 A1 | 1/2018 | |

OTHER PUBLICATIONS

Gerard et al. "Reverse Transcriptase (EC 2.7.7.49)" Chapter 6 (73-93) From: Methods in Molecular Biology, vol. 16: Enzymes of Molecular Biology Edited by: M. M. Burell 1993 Humana Press Inc. Totowa, NJ (Year: 1993).*
Parameswaran et al. "A pyrosequencing-tailored nucleotide barcode design unveils opportunities for large-scale sample multiplexing", Nucleic acid research, vol. 35, No. 19, published Oct. 11, 2007 (Year: 2007).*
International Search Report and Written Opinion in PCT/US2019/015638 mailed Jul. 5, 2019; 15 pages.
Lan, F. et al.; "Droplet barcoding for massively parallel single-molecule deep sequencing"; *Nature Communications*; vol. 7, No. 11784; Jun. 29, 2016; pp. 1-10.
Extended European Search Report from EP 19747263.2 mailed Sep. 28, 2021; 7 pages.
Griebel, T. et al.; "Modelling and simulating generic RNA-Seq experiments with the flux simulator"; *Nucleic Acids Research*; vol. 40, No. 20; Sep. 7, 2012; pp. 10073-10083.

* cited by examiner

*Primary Examiner* — Nancy J Leith
*Assistant Examiner* — Jessica D Parisi
(74) *Attorney, Agent, or Firm* — Kilpatrick Townsend and Stockton LLP

(57) ABSTRACT

Methods are provided of assessing whether multiple differently-barcoded primers occur within the same partition.

21 Claims, 13 Drawing Sheets

FIG. 2
1) Tagging molecules delivered as single- or double-stranded oligonucleotides in solution
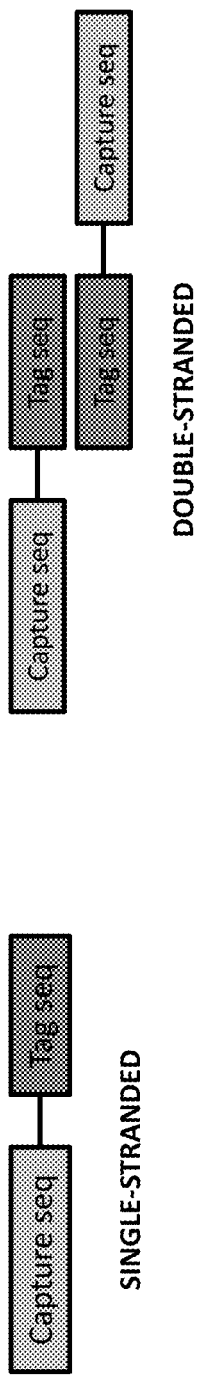
SINGLE-STRANDED
DOUBLE-STRANDED
2) Tagging molecules delivered attached to separate solid particle (bead, PEG, gel, antibody, etc)
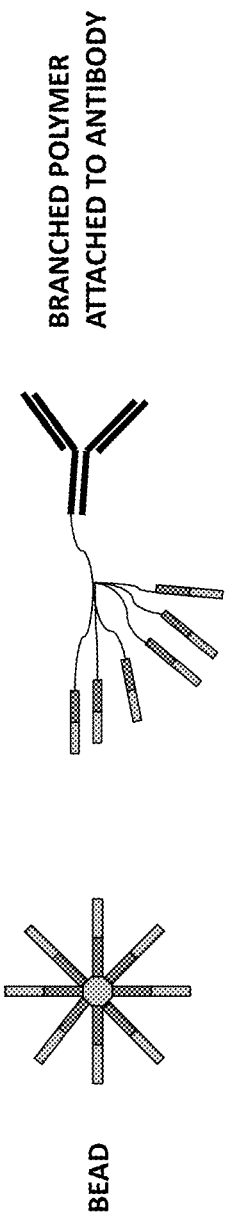
BRANCHED POLYMER ATTACHED TO ANTIBODY
BEAD
3) Tagging molecule built on same particle (e.g. bead) as barcode molecule
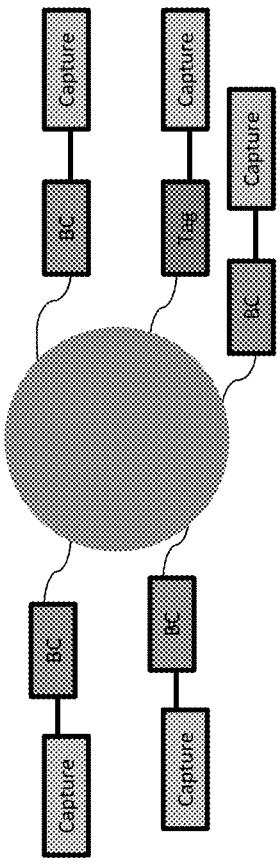

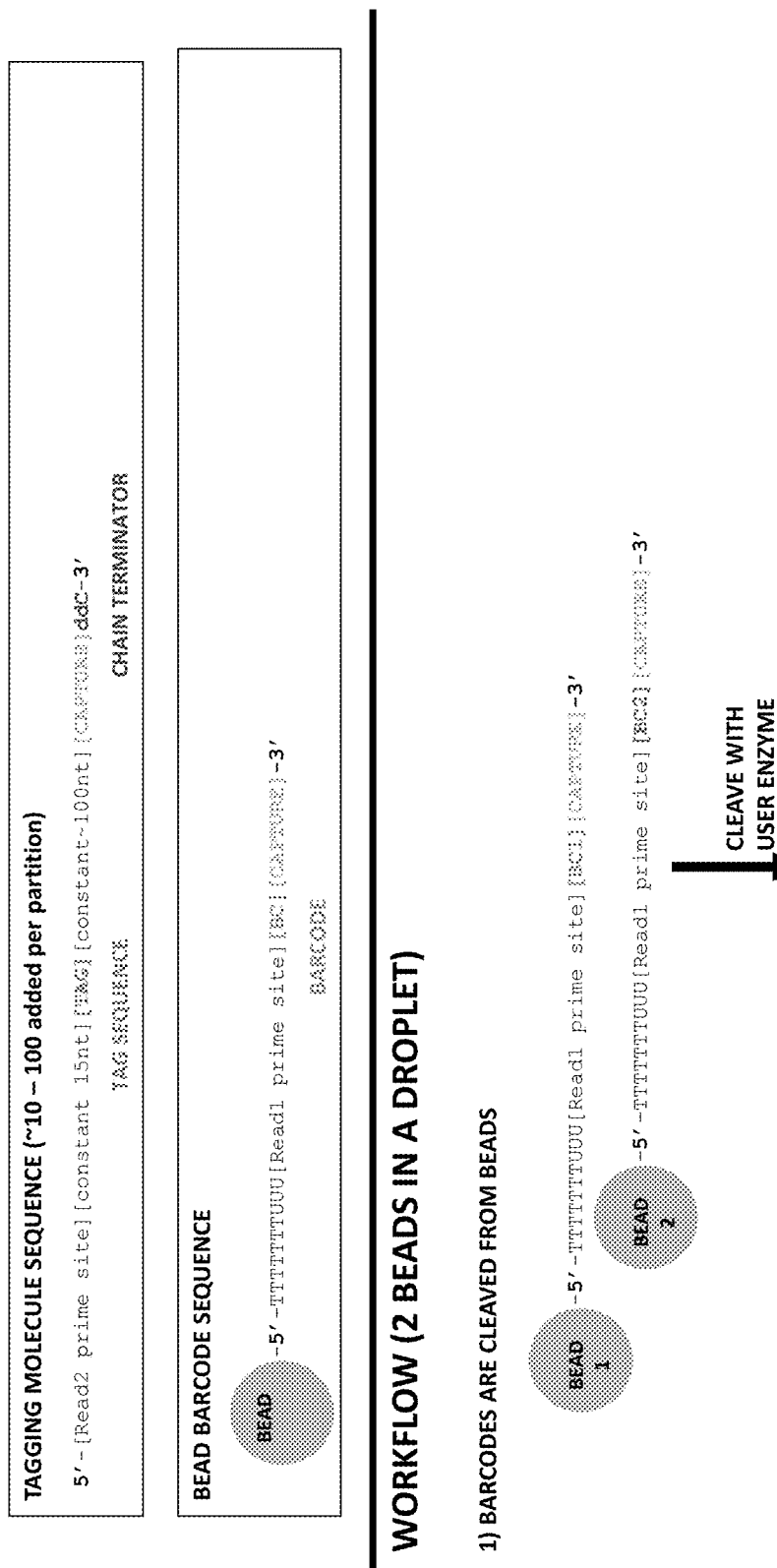

FIG. 5

2) BARCODE 1 CAPTURES TAG MOLECULE, BARCODE EXTENDED, TAG NOT EXTENDED BECAUSE OF ddC

5'-[Read1 prime site][BC1][CAPTURE1][~100nt][TAG1][15nt][Read2 prime site]-3'
                              3'-ddC[CAPTURE1][~100nt][TAG1][15nt][Read2 prime site]-5'

→ EXTEND WITH DNA POLYMERASE

5'-[Read1 prime site][BC1][CAPTURE1][~100nt][TAG1][15nt][Read2 prime site]-3'
3'-          [BC1][CAPTURE1][~100nt][TAG1][15nt][Read2 prime site]-5'

→ MELT, ANNEAL

3) IN FUTURE PCR CYCLE, TAG ANNEALS TO BARCODE 2

5'-[Read1 prime site][BC2][CAPTURE2]-3'
                 3'-ddC[CAPTURE2][~100nt][TAG1][15nt][Read2 prime site]-5'

→ EXTEND WITH DNA POLYMERASE

5'-[Read1 prime site][BC2][CAPTURE2][~100nt][TAG1][15nt][Read2 prime site]-3'
                 3'-ddC[CAPTURE2][~100nt][TAG1][15nt][Read2 prime site]-5'

4) RESULT IS BOTH BARCODES TAGGED BY THE SAME RANDOMER SEQUENCE, READY TO TAKE THROUGH REMAINING SAMPLE PREP TO SEQUENCING

Product 1    5'-[Read1 prime site][BC1][CAPTURE1][~100nt][TAG1][15nt][Read2 prime site]-3'

Product 2    5'-[Read1 prime site][BC2][CAPTURE2][~100nt][TAG1][15nt][Read2 prime site]-3'

FIG. 9

2) BARCODE 1 CAPTURES FORWARD TAG STRAND, BARCODE 2 CAPTURES REVERSE TAG STRAND

```
                                                    3'-[CAPTURE][BC1][Read1 prime site]-5'
5'-[Read2 prime site][constant1 fwd][TAG1 fwd][constant2 fwd]
                    [constant1 rev][TAG1 rev][constant2 rev][Read2 prime site]-5'
                                                    3'-[CAPTURE][BC1]
5'-[Read1 prime site][BC2][CAPTURE]-3'
```

↓ EXTEND WITH POLYMERASE

3) EXTENSION RESULTS IN 2 DOUBLE-STRANDED PRODUCTS

Product 1
5'-[Read1 prime site][BC1][CAPTURE][constant2 rev][TAG1 rev][constant1 fwd][Read2 prime site]-3'
3'-[Read1 prime site][BC1][CAPTURE][constant2 fwd][TAG1 fwd][constant1 rev][Read2 prime site]-5'

Product 2
5'-[Read1 prime site][BC2][CAPTURE][constant1 fwd][TAG1 fwd][constant2 rev][Read2 prime site]-3'
3'-[Read1 prime site][BC2][CAPTURE][constant1 rev][TAG1 rev][constant2 fwd][Read2 prime site]-5'

4) DURING SEQUENCING, IF A TAG (TAG1 fwd) SHOWS UP ASSOCIATED WITH BC1 AND ITS REVERSE COMPLEMENT (TAG1 rev) IS ASSOCIATED WITH BC2, THEN BC1 AND BC2 WERE IN THE SAME DROPLET.

NOTE: Each double-stranded tag can be composed of a random sequence and its reverse-complement, but these could also be made using known sequences and their respective reverse-complements.

FIG. 13

| # Partition ID tags added per partition | % Sequencing reads used on partition ID tags | % Barcodes associated with 1 or more partition ID tag sequences | % Barcodes that do not overlap with at least one other barcode |
|---|---|---|---|
| 0 | 0.001% | 9.1% | 100.000% |
| 10 | 0.022% | 30.4% | 99.995% |
| 100 | 0.320% | 97.1% | 100.000% |
| 1000 | 4.537% | 100.0% | 91.323% |

METHODS AND COMPOSITIONS FOR DECONVOLUTING PARTITION BARCODES

CROSS-REFERENCES TO RELATED APPLICATIONS

The present application claims the benefit of priority to U.S. Provisional Patent Application No. 62/624,400, filed Jan. 31, 2018, the entire contents of which are incorporated herein by reference in its entirety.

BACKGROUND OF THE INVENTION

Beads conjugated to oligonucleotides are used in microfluidic detection applications such as high-throughput sequencing having many different partitions (e.g., droplets). In order to uniquely identify each partition, the beads can be labeled with unique barcode sequences. However, in order to ensure that partitions have only one bead and thus are uniquely labeled by the barcode, bead concentrations are typically adjusted so that only about 1 out of 10 partitions are occupied by a bead. This results in low utilization of the partitions, and increases the amount of sample and reagents that is needed for detection of samples. Increasing bead concentrations would result in higher partition occupancy and greater utilization of partitions. The amount of sample and reagents that are needed for detection of samples would be decreased. Conversely, higher bead concentrations would lead to a greater number of partitions having more than one bead. Thus, some partitioned samples would be labeled by more than one barcode. In some instances, the sample is split between the more than one barcode resulting in a loss of sensitivity per barcode.

BRIEF SUMMARY OF THE INVENTION

In some embodiments, methods of detecting the presence or absence of multiple barcodes in a partition are provided. In some embodiments, the method comprises, forming partitions comprising forward primers comprising a barcode and a capture sequence complementary to the 3' sequence, or reverse complement thereof, of a target nucleic acid, wherein different partitions contain different forward primers comprising different barcode sequences, and a partition ID tag oligonucleotide comprising a reverse complement of the capture sequence and a variable partition ID tag sequence;

in the partitions, hybridizing at least one forward primer to the partition ID tag oligonucleotide to form a hybridized product;

performing amplification on the hybridized product to form amplicons, wherein at least some amplicons are formed from a forward primer and the partition ID tag oligonucleotide; and sequencing the amplicons, wherein if different forward primers form amplicons with the same variable partition ID tag sequence, the different forward primers are considered to be from the same partition, wherein the forward primer and partition ID tag oligonucleotide are linked to the same substrate when delivered to the partitions; or the partition ID tag oligonucleotide has a blocked 3' end such that a polymerase cannot extend the blocked 3' end during amplification; or the partition ID tag oligonucleotide comprises a double-stranded variable partition ID tag sequence and one or two single-stranded 3' ends comprising the reverse complement of the capture sequence.

In some embodiments, the forward primer, the partition ID tag oligonucleotide, or both further comprise a universal adaptor sequence.

In some embodiments, at least some partitions contain the target nucleic acid. In some embodiments, the amplifying also amplifies the target nucleic acid with forward primers and target reverse primers to form an amplification product and the sequencing comprises sequencing the amplification products.

In some embodiments, the amplifying comprises extending the forward primer with a polymerase using the partition ID tag oligonucleotide as a template to form an amplicon comprising the forward primer and the reverse complement of the partition ID tag oligonucleotide.

In some embodiments, in the partition forming step the forward primers are linked to a bead. In some embodiments, multiple copies of partition ID tag oligonucleotides are linked to each other. In some embodiments, the multiple copies are linked to each other through a bead. In some embodiments, during partition forming the forward primer and the partition ID tag oligonucleotide are linked to each other via a cleavable linker and the method further comprises cleaving the cleavable linker before the amplification. In some embodiments, the bead comprises at least 10 (e.g., 100, 1000, 10000) times the number of forward primers compared to partition ID tag oligonucleotides linked to the bead.

In some embodiments, primers are cleaved from the bead before the amplifying.

In some embodiments, the partition ID tag oligonucleotide is single-stranded.

In some embodiments, the variable partition ID tag sequence is double-stranded In some embodiments, 3' ends of each strand of the double stranded variable partition ID tag sequence are linked to a complement of the capture sequence.

In some embodiments, during the partition forming step the partition ID tag oligonucleotide is linked to a solid support.

In some embodiments, the partition ID tag oligonucleotide has a blocked 3' end such that a polymerase cannot extend the blocked 3' end during amplification.

In some embodiments, the partition ID tag oligonucleotide comprises an affinity tag. In some embodiments, the affinity tag is biotin, and antibody, or an apatmer.

In some embodiments, the partitions are droplets.

In some embodiments, the partitions contain on average 2-100000 copies of partition ID tag oligonucleotides per partition. In some embodiments, the partitions contain on average 10-1000 or 100-10,000 copies of partition ID tag oligonucleotides per partition.

In some embodiments, contents of the partitions are combined before the amplifying.

In some embodiments, target reverse primers are present in the partitions.

In some embodiments, target reverse primers are introduced after contents of the partitions are combined.

In some embodiments, the amplification occurs while the hybridized products are within partitions.

In some embodiments, methods of detecting the presence or absence of multiple barcodes in a partition are provided. In some embodiments, the method comprises forming partitions comprising forward primers comprising a barcode and a capture sequence complementary to the 3' sequence, or a reverse complement thereof, of the target nucleic acid, wherein different partitions contain different forward primers comprising different barcode sequences, a partition ID tag oligonucleotide comprising a 5' binding sequence and a 3' variable partition ID tag sequence;

linking the target nucleic acid with the forward primers and the target reverse primers, the target reverse primers having a 3' sequence identical to, or a reverse complement of, the 5' sequence of the target nucleic acid wherein the linking also results in some products in which a forward primer is linked to the partition ID tag oligonucleotide; and sequencing the products, wherein if different forward primers form products with the same variable partition ID tag sequence, the different forward primers are considered to be from the same partition, wherein the forward primer and partition ID tag oligonucleotide are linked to the same bead when delivered to the partitions; or the partition ID tag oligonucleotide has a blocked 3' end such that a polymerase cannot extend the blocked 3' end during amplification; or the partition ID tag oligonucleotide comprises a double-stranded variable partition ID tag sequence and one or two single-stranded 3' ends comprising the reverse complement of the capture sequence.

In some embodiments, at least some partitions contain a target nucleic acid.

In some embodiments, the methods further comprise providing a bridge single strand nucleic acid in the partitions, wherein the bridge single strand nucleic acid comprises from 3' to 5', the 3' sequence of the target nucleic acid and a reverse complement of the 5' binding sequence of the partition ID tag oligonucleotide such that hybridization of a forward primer and the partition ID tag oligonucleotide brings the 3' end of the forward primer adjacent to the 5' end of the partition ID tag oligonucleotide and wherein the 3' end of the forward primer is ligated to the 5' end of the partition ID tag oligonucleotide.

In some embodiments, in the partition forming step the forward primers are linked to a bead. In some embodiments, multiple copies of partition ID tag oligonucleotides linked to each other. In some embodiments, the multiple copies are linked to each other through a bead. In some embodiments, during the partition forming the forward primer and the partition ID tag oligonucleotide are linked to each other via a cleavable linker and the method further comprises cleaving the cleavable linker before the linking. In some embodiments, the bead comprises at least 10 (e.g., 100, 1000, 10000) times the number of forward primers compared to partition ID tag oligonucleotides linked to the bead.

In some embodiments, primers are cleaved from the bead before the linking.

In some embodiments, the partition ID tag oligonucleotide is single-stranded.

In some embodiments, the variable partition ID tag sequence is double-stranded.

In some embodiments, during the partition forming step the partition ID tag oligonucleotide is linked to a solid support.

In some embodiments, the partition ID tag oligonucleotide has a blocked 3' end such that a polymerase in the amplifying cannot extend the blocked 3' end.

In some embodiments, the partition ID tag oligonucleotide comprises an affinity tag. In some embodiments, the affinity tag is biotin, an antibody, or an aptamer.

In some embodiments, the partitions are droplets.

In some embodiments, the partitions contain on average 2-100,000 copies of partition ID tag oligonucleotides per partition. In some embodiments, the partitions contain on average 10-1000 or 100-10,000 copies of partition ID tag oligonucleotides per partition.

In some embodiments, a plurality of partitions are provided. In some embodiments, the partitions comprise: one or more forward primers comprising a barcode and a capture sequence complementary to the 3' sequence, or a reverse complement thereof, of the target nucleic acid, wherein different partitions contain different forward primers comprising different barcode sequences, and a partition ID tag oligonucleotide comprising a complement of the capture sequence and a variable partition ID tag sequence.

In some embodiments, at least some partitions contain a target nucleic acid.

In some embodiments, the partitions further comprise target reverse primers having a 3' sequence identical to, or a reverse complement of, the 5' sequence of the target nucleic acid.

In some embodiments, the forward primers are linked to a bead.

In some embodiments, multiple partition ID tag oligonucleotides linked to each other. In some embodiments, the multiple partition ID tag oligonucleotides are linked to each other through a bead. In some embodiments, the forward primer and the partition ID tag oligonucleotide are linked to each other via a cleavable linker and the method further comprises cleaving the cleavable linker before the amplifying. In some embodiments, the bead comprises at least 10 (e.g., 100, 1000, 10000) times the number of forward primers compared to partition ID tag oligonucleotides linked to the bead.

In some embodiments, primers are cleaved from the bead before the amplifying.

In some embodiments, the partition ID tag oligonucleotide is single-stranded.

In some embodiments, the variable partition ID tag sequence is double-stranded.

In some embodiments, 3' ends of each strand of the double stranded variable partition ID tag sequence are linked to a complement of the capture sequence.

In some embodiments, the partition ID tag oligonucleotide is linked to a solid support.

In some embodiments, the partition ID tag oligonucleotide has a blocked 3' end such that a polymerase in the amplifying cannot extend the blocked 3' end.

In some embodiments, the partition ID tag oligonucleotide comprises an affinity tag. In some embodiments, the affinity tag is biotin, an antibody, or an aptamer.

In some embodiments, the partitions further comprise target reverse primers.

In some embodiments, the partitions are droplets.

In some embodiments, the partitions contain on average 2-100000 copies of partition ID tag oligonucleotides per partition.

In some embodiments, the partitions contain on average 10-1000 or 100-10,000 copies of partition ID tag oligonucleotides per partition.

In some embodiments, the plurality comprises at least 100 (e.g., at least 1000, 10000, 100000) partitions.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, analytical chemistry, and nucleic acid chemistry and hybridization described below are those well-known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document.

A "partition ID tag" refers to a nucleic acid sequence or unique combination of sequences that is in a particular partition. The partition ID tag can be introduced to each partition as part of a longer polynucleotide sequence, for example having a capture sequence or a complement thereof on the 3' end of the polynucleotide for later linkage to the forward primer. The partition ID tag sequence can be of any length as desired. As non-limiting the examples, the partition ID tag can be for example 4-50 or more nucleotides in length and can be contiguous or non-contiguous (e.g., can be in two or more portions separated by a non-tag (e.g., spacer) sequence). Each partition will generally include a different partition ID tag, which can be for example generated randomly or non-randomly.

The term "amplification reaction" refers to any in vitro method for multiplying the copies of a target sequence of nucleic acid in a linear or exponential manner. Such methods include, but are not limited to, polymerase chain reaction (PCR); DNA ligase chain reaction (LCR); QBeta RNA replicase and RNA transcription-based amplification reactions (e.g., amplification that involves T7, T3, or SP6 primed RNA polymerization), such as the transcription amplification system (TAS), nucleic acid sequence based amplification (NASBA), and self-sustained sequence replication (3SR); single-primer isothermal amplification (SPIA), loop mediated isothermal amplification (LAMP), strand displacement amplification (SDA); multiple displacement amplification (MDA); rolling circle amplification (RCA); as well as others known to those of skill in the art. See, e.g., Fakruddin et al., *J. Pharm Bioallied Sci.* 2013 5(4):245-252.

"Amplifying" refers to a step of submitting a solution to conditions sufficient to allow for amplification of a polynucleotide if all of the components of the reaction are intact. Components of an amplification reaction include, e.g., primers, a polynucleotide template, polymerase, nucleotides, and the like. The term "amplifying" typically refers to an "exponential" increase in target nucleic acid. However, "amplifying" as used herein can also refer to linear increases in the numbers of a select target sequence of nucleic acid, such as is obtained with cycle sequencing or linear amplification.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990. Exemplary PCR reaction conditions typically comprise either two or three step cycles. Two step cycles have a denaturation step followed by a hybridization/elongation step. Three step cycles comprise a denaturation step followed by a hybridization step followed by a separate elongation step.

A "primer" refers to a polynucleotide sequence that hybridizes to a sequence on a target nucleic acid and optionally serves as a point of initiation of nucleic acid synthesis. Primers can be of a variety of lengths. In some embodiments, a primer is less than 100 or 50 nucleotides in length, e.g., from about 10 to about 900, from about 15 to about 80, or from about 30-85 to about 30 nucleotides in length. The length and sequences of primers for use in an amplification reaction (e.g., PCR) can be designed based on principles known to those of skill in the art; see, e.g., PCR Protocols: A Guide to Methods and Applications, Innis et al., eds, 1990. The primer can include or be completely formed from DNA, RNA or non-natural nucleotides. In some embodiments, a primer comprises one or more modified and/or non-natural nucleotide bases. In some embodiments, a primer comprises a label (e.g., a detectable label).

A nucleic acid, or portion thereof, "hybridizes" to another nucleic acid under conditions such that non-specific hybridization is minimal at a defined temperature in a physiological buffer. In some cases, a nucleic acid, or portion thereof, hybridizes to a conserved sequence shared among a group of target nucleic acids. In some cases, a primer, or portion thereof, can hybridize to a primer binding site if there are at least about 6, 8, 10, 12, 14, 16, or 18 contiguous complementary nucleotides, including "universal" nucleotides that are complementary to more than one nucleotide partner. Alternatively, a primer, or portion thereof, can hybridize to a primer binding site if there are fewer than 1 or 2 complementarity mismatches over at least about 12, 14, 16, or 18 contiguous complementary nucleotides. In some embodiments, the defined temperature at which specific hybridization occurs is room temperature. In some embodiments, the defined temperature at which specific hybridization occurs is higher than room temperature. In some embodiments, the defined temperature at which specific hybridization occurs is at least about 37, 40, 42, 45, 50, 55, 60, 65, 70, 75, or 80° C.

As used herein, "nucleic acid" refers to DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, points of attachment and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications including but not limited to capping with a fluorophore (e.g., quantum dot) or another moiety.

As used herein, the term "partitioning" or "partitioned" refers to separating a sample into a plurality of portions, or "partitions." Partitions can be solid or fluid. In some embodiments, a partition is a solid partition, e.g., a microchannel or a well (i.e., in a multi-well microtiter dish). In some embodiments, a partition is a fluid partition, e.g., a droplet. In some embodiments, a fluid partition (e.g., a droplet) is a mixture of immiscible fluids (e.g., water and oil). In some embodiments, a fluid partition (e.g., a droplet) is an aqueous droplet that is surrounded by an immiscible carrier fluid (e.g., oil).

As used herein, a "barcode" is a short nucleotide sequence (e.g., at least about 4, 6, 8, 10, 12, 14, 16, 18, 20, 25, 30 or more nucleotides long) that identifies a molecule to which it is conjugated. In some embodiments, a barcode is used to identify molecules in a partition. Such a partition-specific barcode should be unique for that partition as compared to barcodes present in other partitions. For example, partitions containing target RNA from single cells can be subjected to reverse transcription conditions using primers that contain a different partition-specific barcode sequence in each partition, thus incorporating a copy of a unique "cellular barcode" into the reverse transcribed nucleic acids of each partition. Thus, nucleic acid from each cell can be distinguished from nucleic acid of other cells due to the unique "cellular barcode." In some embodiments, a barcode is present on oligonucleotides conjugated to a particle, wherein the "particle barcode" is shared by (e.g., identical or substantially identical amongst) all, or substantially all, of the oligonucleotides conjugated to that particle.

In some embodiments, a barcode is provided in a substrate. In some embodiments, a substrate comprises a single barcode sequence. In some embodiments, a substrate comprises repeating clonal barcode sequences. As used herein, a "substrate comprising repeating clonal barcode sequences" refers to a composition that contains a plurality of identical barcode sequences that are physically connected to each other (e.g., in a hairpin molecule, a linear nucleic acid polymer, or a circular nucleic acid polymer as tandem repeating barcode sequences separated by a cleavable linker between each repeating sequence) or that are sequestered from other components when delivered to a partition (e.g., encapsulated within a droplet that is delivered to a partition). In some embodiments, individual barcode sequences are released from the substrate or released from a repeating clonal barcode sequence (e.g., released from the hairpin, linear nucleic acid polymer, or circular nucleic acid polymer by cleaving the polymer at the cleavable linkers, or released from the droplet by breaking the droplet) in a partition, and are associated with a particle in the partition, for example, by annealing the clonal barcode sequence to an oligonucleotide on the partition or by ligating the clonal barcode sequence to an oligonucleotide on the partition.

BRIEF DESCRIPTION OF THE DRAWINGS

FIG. 2 depicts alternative configurations of partition ID tag delivery to a partition. In all of the embodiments depicted, the capture sequence is linked to the partition ID tag sequence. The top section of the figure illustrates that the tagging sequence can be single-stranded or double stranded (e.g., partially double-stranded at the partition ID tag sequence while being single-stranded at the capture sequence). The middle section of the figure depicts that the tagging sequence can be delivered to a partition linked to a solid support or linked to another molecule. The lower section of the figures shows that the barcode sequence and the tagging sequence can be delivered as part of the same molecule (later to be separated) and in some embodiments, is optionally further linked to a solid support.

FIG. 3 depicts an aspect in which single-stranded partition ID tags are in solution with multiple barcode beads. The circle indicates a partition, in which the depicted oligonucleotide capture and sample preparation steps result in covalently combining barcodes to target and tag molecules. The partition is subsequently combined with contents of other partitions (e.g., by breaking an emulsion) for downstream sample preparation and/or analysis. While FIG. 3 depicts a single TAG1 Oligonucleotide interacting first with BC1 and later with BC2, it will be appreciated that in some embodiments, there will be multiple copies of the same partition ID tag in the partition such that different copies of partition ID tags interact with the different bead forward primers.

FIG. 4 depicts a first part of a single-stranded partition ID tag example workflow containing multiple PCR cycles (allowing the same partition ID tag sequence to combine with multiple forward primer barcode sequences). As depicted, the partition ID tag has a 3' dideoxynucleotide preventing it from being extended by a polymerase. The depicted workflow shows two beads having different barcodes (BC1 and BC2) in the same partition (as depicted a droplet). The forward primers linked to the beads are cleaved to release the barcoded forward primers.

FIG. 5 is a continuation of the workflow from FIG. 4. Part 2) depicts extension of the forward primer having BC1 using the partition ID tag as a template. In part 3), forward primer having BC2 is extended using the partition ID tag as a template. As shown in part 4), two different forward barcodes being associated with the same partition ID tag (depicted as TAG1) indicates that two forward primers were in the same partition.

FIG. 9 depicts continuation of the workflow of FIG. 8. In part 2 of the workflow, barcoded forward primers hybridize via the capture sequences of the partition ID tag and extension in part 3 results in amplicons in which the two different barcodes (BC1 and BC2) are each associated with the tag sequence or a reverse complement thereof.

FIG. 13 shows barcode detection data using partition ID tag scheme shown in FIG. 6

DETAILED DESCRIPTION OF THE INVENTION

Introduction

A finite amount of entities can be distributed across a certain amount of partitions. This means one could encounter partitions with 0, 1, 2, 3, etc. entities within a particular partition. Especially at lower concentrations (e.g., <20 entities per partition on average) the distribution of what percentage of partitions contains what number of entities follows a Poisson distribution. In some applications the entities to be partitioned are beads and the partitions themselves are droplets.

A partition barcode or mixture thereof can be used to label molecules of interest (e.g., mRNA, cDNA, DNA, etc.) within a certain partition. Ideally one wants to only have one barcode per partition. Since that is not always feasible, methods described herein provide methods to determine which partition barcode or combination of barcodes were present within each partition. The methods described herein provide for addition of partition ID tags to partitions.

These partition ID tags mark ("tag") the barcodes. Accordingly, barcodes occupying the same partition will be tagged by the same partition ID or combination of partitions IDs.

The inventors have discovered how to detect the presence in partitions of multiple beads that are loaded with bead-specific barcode primers. The presence of more than one differently-barcoded primer (e.g., two differently-barcoded forward primers linked to different beads in the same partition) interfere with sequence analysis and quantification because different barcodes are assumed to be from different partitions when in fact some fraction of the barcodes occur together (for example as a function of a Gaussian distribution). By being able to detect which barcodes occurred in the same partitions, one can either deconvolute (i.e., determine that multiple barcodes are from the same partition and account for that in the sequencing analysis) and use the data from such combinations or disregard (e.g., discard) data from such partitions, leaving the remaining data more "clean" from background effects. The inventors have discovered that one can introduce partition ID tag sequences into partitions and can associate them with some fraction of the forward primers in a partition. By sequencing the products of these associations, one can detect those partitions with multiple differently-barcoded forward primers because they will be associated with the same partition ID tags (or complement thereof). A number of ways of delivering and associating the partition ID tags and the forward primers are described herein.

Figure 1:
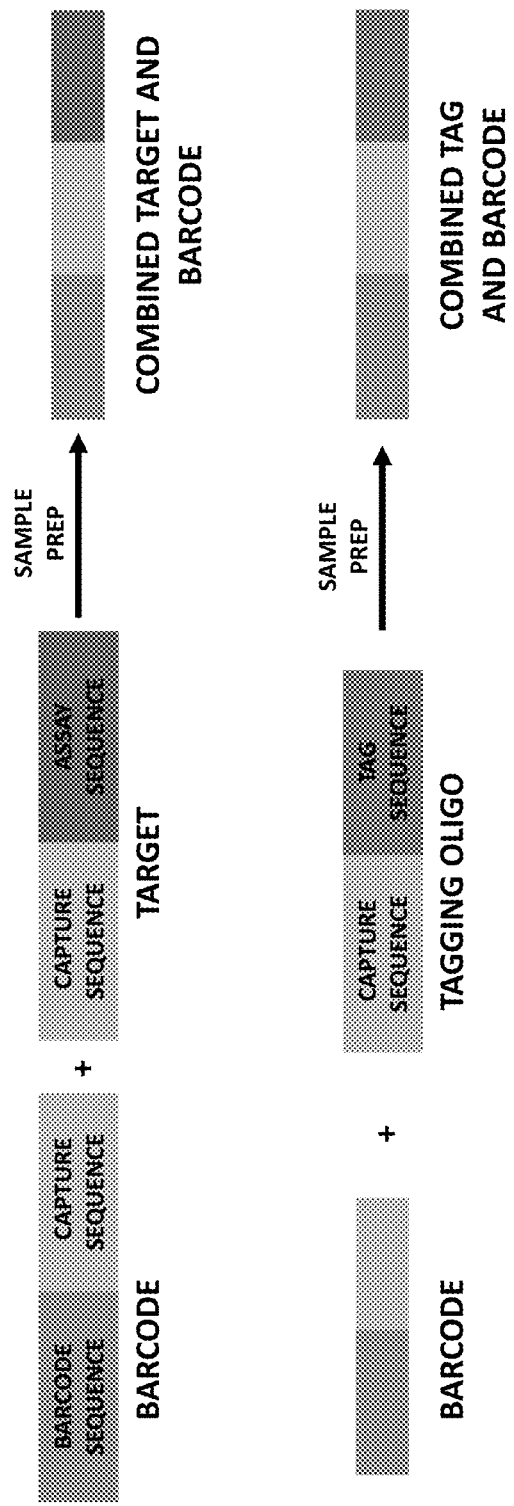
FIG. 1 depicts an aspect of using tagging to detect multiple barcodes in a partition. The top section depicts barcoding of a target sequence where a barcode (also referred to herein as a "forward primer") is associated with a target nucleic acid sequence via a capture sequence. As an example, the capture sequence linked to the barcode can be complementary to the capture sequence of the target. The resulting product comprises the barcode, capture sequence and target sequence. The lower box depicts tagging of a barcode sequence. In this aspect the forward primer barcode becomes associated with a partition ID tag via interaction of capture sequences on the barcode oligonucleotide (forward primer) and the tagging oligonucleotide. The resulting product of this reaction is the barcode is covalently linked to the partition ID tag via the capture sequence. The depicted reactions could occur side-by-side in the same partition, with the same or varied workflows. Products of these reactions could be further prepared for analysis simultaneously, using the same workflow, or separated and taken through different workflows. While the figures illustrate oligonucleotides without PCR handle sequences, it will be understood that in some embodiments, such sequences can be present. PCR handle sequences can be included, for example as part of the forward primer, target reverse primer and reverse tag primer, allowing for universal sequences for later amplification of the resulting products.

FIG. 1 depicts an embodiment in which a target sequence is barcoded by a partition barcoding primer present in a partition (top portion of figure). In the same partition, a partition ID tag oligonucleotide is linked to some copies of the partition barcoding primer to link the partition ID tag sequence of the partition ID tag oligonucleotide to the partition barcode, thereby allowing for detection of multiple barcodes (if present) in a partition.

Figure 3:
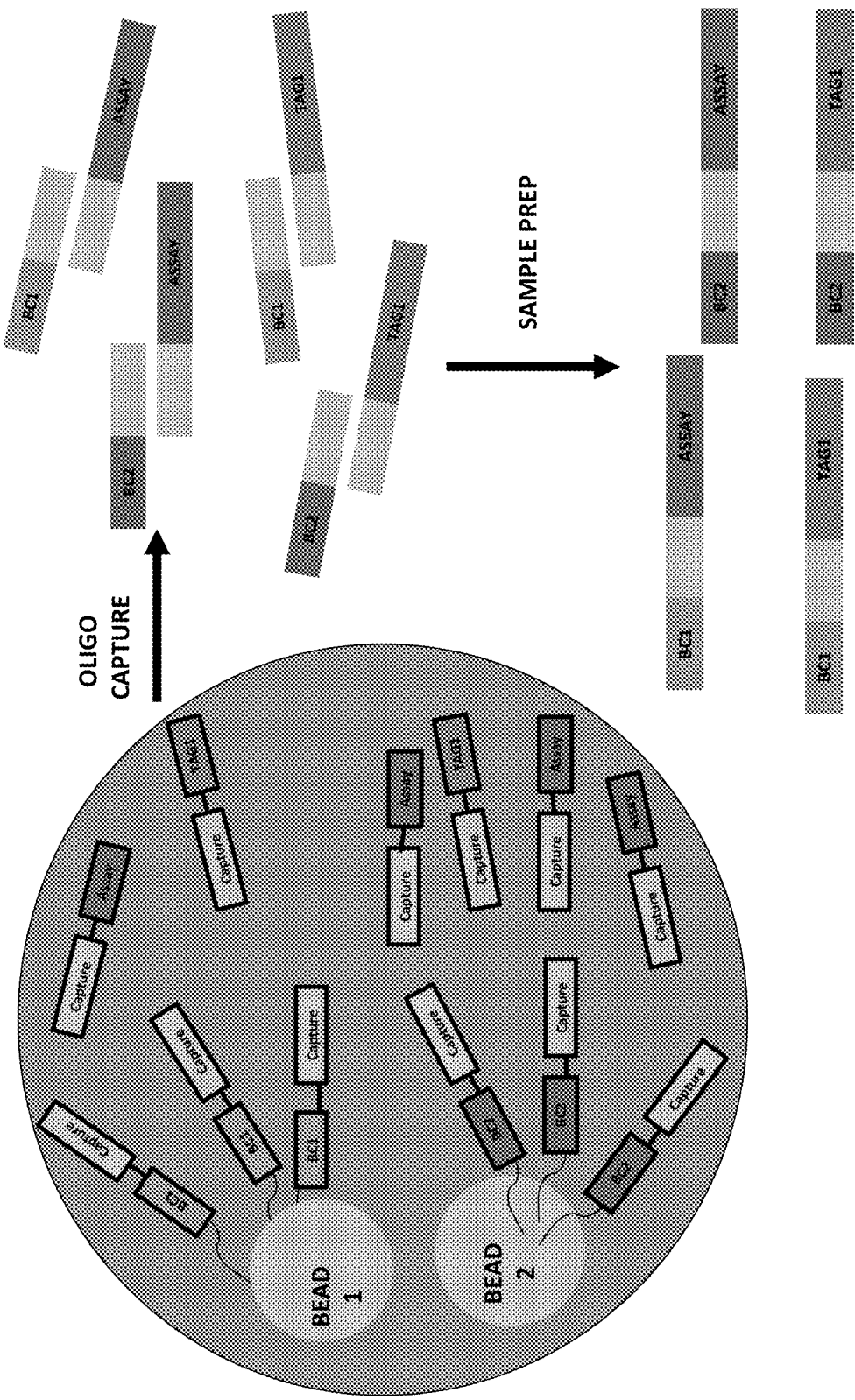

FIG. 3 depicts an aspect in which two forward primers with different barcodes are in the same partition. While the forward primers are depicted as linked to beads, that aspect is not required. Included in the partition are some copies of a single-stranded partition ID tag oligonucleotide (having capture and partition ID tag sequences) as well as target nucleic acids (having capture and assay (e.g., a sequence to be determined) sequences). Some copies of the forward primer are linked via the capture sequences to the target nucleic acids and other copies of the forward primers are linked via the capture sequence to the partition ID tag oligonucleotides. The linkage of different barcodes (BC1 and BC2) with the same partition ID tag sequence (TAG1) indicates two different forward primers (associated with BC1 and BC2) were present in the same partition.

Partitions containing forward primers and in some embodiments also target reverse primers for amplification of a target nucleic acid are provided. In many cases, it is convenient to deliver to the partitions, or to form the partitions around, a solid support (e.g., a bead) linked to the barcoded forward primer, wherein the goal is a 1:1 distribution of beads linked to forward primers and partitions. However, due to Gaussian distributions, some partitions will contain more than one forward primer bead. Methods and compositions for partitioning are described, for example, in published patent applications WO 2010/036,352, US 2010/0173,394, US 2011/0092,373, and US 2011/0092,376, the contents of each of which are incorporated herein by reference in the entirety. The plurality of partitions can be in a plurality of emulsion droplets, or a plurality of microwells, etc.

In some embodiments, one or more reagents are added during droplet formation or to the droplets after the droplets are formed. Methods and compositions for delivering reagents to one or more partitions include microfluidic methods as known in the art; droplet or microcapsule combining, coalescing, fusing, bursting, or degrading (e.g., as described in U.S. 2015/0027,892; US 2014/0227,684; WO 2012/149,042; and WO 2014/028,537); droplet injection methods (e.g., as described in WO 2010/151,776); and combinations thereof.

As described herein, the partitions can be picowells, nanowells, or microwells. The partitions can be pico-, nano-, or micro-reaction chambers, such as pico, nano, or microcapsules. The partitions can be pico-, nano-, or microchannels. The partitions can be droplets, e.g., emulsion droplets.

In some embodiments, the partitions are droplets. In some embodiments, a droplet comprises an emulsion composition, i.e., a mixture of immiscible fluids (e.g., water and oil). In some embodiments, a droplet is an aqueous droplet that is surrounded by an immiscible carrier fluid (e.g., oil). In some embodiments, a droplet is an oil droplet that is surrounded by an immiscible carrier fluid (e.g., an aqueous solution). In some embodiments, the droplets described herein are relatively stable and have minimal coalescence between two or more droplets. In some embodiments, less than 0.0001%, 0.0005%, 0.001%, 0.005%, 0.01%, 0.05%, 0.1%, 0.5%, 1%, 2%, 3%, 4%, 5%, 6%, 7%, 8%, 9%, or 10% of droplets generated from a sample coalesce with other droplets. The emulsions can also have limited flocculation, a process by which the dispersed phase comes out of suspension in flakes. In some cases, such stability or minimal coalescence is maintained for up to 4, 6, 8, 10, 12, 24, or 48 hours or more (e.g., at room temperature, or at about 0, 2, 4, 6, 8, 10, or 12° C.). In some embodiments, the droplet is formed by flowing an oil phase through an aqueous sample or reagents.

The oil phase can comprise a fluorinated base oil which can additionally be stabilized by combination with a fluorinated surfactant such as a perfluorinated polyether. In some embodiments, the base oil comprises one or more of a HFE 7500, FC-40, FC-43, FC-70, or another common fluorinated oil. In some embodiments, the oil phase comprises an anionic fluorosurfactant. In some embodiments, the anionic fluorosurfactant is Ammonium Krytox (Krytox-AS), the ammonium salt of Krytox FSH, or a morpholino derivative of Krytox FSH. Krytox-AS can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of Krytox-AS is about 1.8%. In some embodiments, the concentration of Krytox-AS is about 1.62%. Morpholino derivative of Krytox FSH can be present at a concentration of about 0.1%, 0.2%, 0.3%, 0.4%, 0.5%, 0.6%, 0.7%, 0.8%, 0.9%, 1.0%, 2.0%, 3.0%, or 4.0% (w/w). In some embodiments, the concentration of morpholino derivative of Krytox FSH is about 1.8%. In some embodiments, the concentration of morpholino derivative of Krytox FSH is about 1.62%.

In some embodiments, the oil phase further comprises an additive for tuning the oil properties, such as vapor pressure, viscosity, or surface tension. Non-limiting examples include perfluorooctanol and 1H,1H,2H,2H-Perfluorodecanol. In some embodiments, 1H,1H,2H,2H-Perfluorodecanol is added to a concentration of about 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.25%, 1.50%, 1.75%, 2.0%, 2.25%, 2.5%, 2.75%, or 3.0% (w/w). In some embodiments, 1H,1H,2H,2H-Perfluorodecanol is added to a concentration of about 0.18% (w/w).

In some embodiments, the emulsion is formulated to produce highly monodisperse droplets having a liquid-like interfacial film that can be converted by heating into microcapsules having a solid-like interfacial film; such microcapsules can behave as bioreactors able to retain their contents through an incubation period. The conversion to microcapsule form can occur upon heating. For example, such conversion can occur at a temperature of greater than about 40°, 50°, 60°, 70°, 80°, 90°, or 95° C. During the heating process, a fluid or mineral oil overlay can be used to prevent evaporation. Excess continuous phase oil can be removed prior to heating, or left in place. The microcapsules can be resistant to coalescence and/or flocculation across a wide range of thermal and mechanical processing.

Following conversion of droplets into microcapsules, the microcapsules can be stored at about −70°, −20°, 0°, 3°, 4°, 5°, 6°, 7°, 8°, 9°, 10°, 15°, 20°, 25°, 30°, 35°, or 40° C. In some embodiments, these capsules are useful for storage or transport of partition mixtures. For example, samples can be collected at one location, partitioned into droplets containing enzymes, buffers, and/or primers or other probes, optionally one or more polymerization reactions can be performed, the partitions can then be heated to perform microencapsulation, and the microcapsules can be stored or transported for further analysis.

In some embodiments, the sample is partitioned into, or into at least, 500 partitions, 1000 partitions, 2000 partitions, 3000 partitions, 4000 partitions, 5000 partitions, 6000 partitions, 7000 partitions, 8000 partitions, 10,000 partitions, 15,000 partitions, 20,000 partitions, 30,000 partitions, 40,000 partitions, 50,000 partitions, 60,000 partitions, 70,000 partitions, 80,000 partitions, 90,000 partitions, 100,000 partitions, 200,000 partitions, 300,000 partitions, 400,000 partitions, 500,000 partitions, 600,000 partitions, 700,000 partitions, 800,000 partitions, 900,000 partitions, 1,000,000 partitions, 2,000,000 partitions, 3,000,000 partitions, 4,000,000 partitions, 5,000,000 partitions, 10,000,000 partitions, 20,000,000 partitions, 30,000,000 partitions, 40,000,000 partitions, 50,000,000 partitions, 60,000,000 partitions, 70,000,000 partitions, 80,000,000 partitions, 90,000,000 partitions, 100,000,000 partitions, 150,000,000 partitions, or 200,000,000 partitions.

In some embodiments, the droplets that are generated are substantially uniform in shape and/or size. For example, in some embodiments, the droplets are substantially uniform in average diameter. In some embodiments, the droplets that are generated have an average diameter of about 0.001 microns, about 0.005 microns, about 0.01 microns, about 0.05 microns, about 0.1 microns, about 0.5 microns, about 1 microns, about 5 microns, about 10 microns, about 20 microns, about 30 microns, about 40 microns, about 50 microns, about 60 microns, about 70 microns, about 80 microns, about 90 microns, about 100 microns, about 150 microns, about 200 microns, about 300 microns, about 400 microns, about 500 microns, about 600 microns, about 700 microns, about 800 microns, about 900 microns, or about 1000 microns. In some embodiments, the droplets that are generated have an average diameter of less than about 1000 microns, less than about 900 microns, less than about 800 microns, less than about 700 microns, less than about 600 microns, less than about 500 microns, less than about 400 microns, less than about 300 microns, less than about 200 microns, less than about 100 microns, less than about 50 microns, or less than about 25 microns. In some embodiments, the droplets that are generated are non-uniform in shape and/or size.

In some embodiments, the droplets that are generated are substantially uniform in volume. For example, the standard deviation of droplet volume can be less than about 1 picoliter, 5 picoliters, 10 picoliters, 100 picoliters, 1 nL, or less than about 10 nL. In some cases, the standard deviation of droplet volume can be less than about 10-25% of the average droplet volume. In some embodiments, the droplets that are generated have an average volume of about 0.001 nL, about 0.005 nL, about 0.01 nL, about 0.02 nL, about 0.03 nL, about 0.04 nL, about 0.05 nL, about 0.06 nL, about 0.07 nL, about 0.08 nL, about 0.09 nL, about 0.1 nL, about 0.2 nL, about 0.3 nL, about 0.4 nL, about 0.5 nL, about 0.6 nL, about 0.7 nL, about 0.8 nL, about 0.9 nL, about 1 nL, about 1.5 nL, about 2 nL, about 2.5 nL, about 3 nL, about 3.5 nL, about 4 nL, about 4.5 nL, about 5 nL, about 5.5 nL, about 6 nL, about 6.5 nL, about 7 nL, about 7.5 nL, about 8 nL, about 8.5 nL, about 9 nL, about 9.5 nL, about 10 nL, about 11 nL, about 12 nL, about 13 nL, about 14 nL, about 15 nL, about 16 nL, about 17 nL, about 18 nL, about 19 nL, about 20 nL, about 25 nL, about 30 nL, about 35 nL, about 40 nL, about 45 nL, or about 50 nL.

In some embodiments, the method comprises partitioning a sample comprising one or more target nucleic acids into a plurality of partitions. In some embodiments, the sample comprising target nucleic acids comprises DNA, RNA, or a combination or hybrid thereof. In some embodiments, the sample comprising target nucleic acids comprises genomic DNA or DNA from a subset of a genome (e.g., selected genes that may harbor mutations for a particular population, such as individuals who are predisposed for a particular type of cancer). In some embodiments, the sample comprises contiguity preserved genomic DNA that has been fragmented but retain contiguity by linkage of a protein (e.g., a Tn5 transposase (tagmentase)) to the DNA fragment ends. In some embodiments, the sample comprising target nucleic acids comprises cDNA. In some embodiments, the sample comprising target nucleic acids comprises exome DNA (i.e., a subset of whole genomic DNA enriched for transcribed sequences which contains the set of exons in a genome) or transcriptome DNA (i.e., the set of all mRNA or "transcripts" produced in a cell or population of cells). In some embodiments, the sample comprising target nucleic acids comprises long fragment DNA (e.g., DNA having a length of at least about 300, 400, 500, 600, 700, 800, 1000, or more bases, or base pairs for double-stranded DNA). In some embodiments, the sample comprising target nucleic acids comprises RNA, e.g., mRNA or lncRNA. In some embodiments, the target nucleic acids are double stranded. In some embodiments, the target nucleic acids are single stranded. In some embodiments, the sample comprises target nucleic acids isolated from tissue, cells, or a single-cell sample.

In some embodiments, the sample comprising target nucleic acids is a biological sample. Biological samples can be obtained from any biological organism, e.g., an animal, plant, fungus, pathogen (e.g., bacteria or virus), or any other organism. In some embodiments, the biological sample is from an animal, e.g., a mammal (e.g., a human or a non-human primate, a cow, horse, pig, sheep, cat, dog, mouse, or rat), a bird (e.g., chicken), or a fish. A biological sample can be any tissue or bodily fluid obtained from the biological organism, e.g., blood, a blood fraction, or a blood product (e.g., serum, plasma, platelets, red blood cells, and the like), sputum or saliva, tissue (e.g., kidney, lung, liver, heart, brain, nervous tissue, thyroid, eye, skeletal muscle, cartilage, or bone tissue); cultured cells, e.g., primary cultures, explants, and transformed cells, stem cells, stool, urine, etc. In some embodiments, the sample is a sample comprising cells. In some embodiments, the sample is a single-cell sample.

In some embodiments, the methods described herein are used for single cell analysis. Accordingly, in some embodiments, target nucleic acids from a single cell are partitioned into a plurality of partitions. In some embodiments, target nucleic acids from a biological sample containing a plurality of cells are extracted and partitioned such that individual partitions contain nucleic acid from less than one, one, or a plurality of cells.

As noted above, the partitions will include a forward primer for amplification or other detection of a target nucleic acid. In some embodiments, the forward primer is linked to a bead or other solid support when provided in partitions. Due to statistical distributions, while many partitions will contain only one forward primer (or multiple copies of only one forward primer) other partitions will include forward primers having different sequences (e.g., different barcodes). In some embodiments, beads or other solid supports that are conjugated to barcode-labeled forward primers are used in the methods, partition libraries, and kits described herein. In some embodiments, the bead comprises a solid support surface having a plurality of oligonucleotide primers conjugated thereon. In some embodiments, the bead comprises at least about 10, 50, 100, 500, 1000, 5000, 10,000, 50,000, 100,000, 500,000, 1,000,000, 5,000,000, 10,000,000, $10^8$, $10^9$, $10^{10}$ or more identical forward primers conjugated thereto. In some embodiments, the forward primers are double-stranded. In some embodiments, the forward primers are single-stranded.

In some embodiments, the forward primers comprise a barcode sequence, wherein at least a majority, substantially all, or all of the plurality of forward primers conjugated to a solid support surface comprise the same barcode sequence. In some embodiments, the barcode is a sequence of about 6 to about 400 nucleotides, e.g., about 6-25, about 10-24, about 8-20, about 8-18, about 10-20, about 10-18, or about 12-20 nucleotides. In some embodiments, the barcode is a sequence of at least about 10 nucleotides. In some embodiments, the oligonucleotide primers conjugated to a particular bead comprise a barcode sequence that is the same or substantially the same among the plurality of oligonucleotides on a bead, but unique or substantially unique as compared to the plurality of oligonucleotides on other beads.

The forward primers also comprise a capture sequence, typically at the 3' end of the forward primer, that hybridizes under the conditions of the assay with a target sequence or a reverse complement thereof. The target sequence can be 100% complementary or partially (e.g., at least 95%, 90%, 80%, etc.) complementary depending on the desired results and conditions. In some embodiments, the capture sequence is a sequence of about 6 to about 20 nucleotides, e.g., about 6-16, about 6-14, about 8-20, about 8-18, about 10-20, about 10-18, or about 12-20 nucleotides. In some embodiments, the capture sequence is a sequence of at least about 6 or 10 nucleotides. For example, the forward primers can comprise a capture sequence complementary to the 3' sequence or a reverse complement thereof, of a target nucleic acid. In addition, the forward primer can include one or more other sequences. For example, in some embodiments, the forward primers each include a unique molecular identifier (UMI) sequence so each copy can be separately tracked and counted.

The term "bead" refers to any solid support that can be in a partition, e.g., a small particle or other solid support. In some embodiments, the beads comprise polyacrylamide. For example, in some embodiments, the beads incorporate barcode oligonucleotides into the gel matrix through an acrydite chemical modification attached to each oligonucleotide. Exemplary beads can also be hydrogel beads. In some cases, the hydrogel is in sol form. In some cases, the hydrogel is in gel form. An exemplary hydrogel is an agarose hydrogel. Other hydrogels include, but are not limited to, those described in, e.g., U.S. Pat. Nos. 4,438,258; 6,534,083;

8,008,476; 8,329,763; U.S. Patent Appl. Nos. 2002/0,009,591; 2013/0,022,569; 2013/0,034,592; and International Patent Publication Nos. WO/1997/030092; and WO/2001/049240.

Methods of linking oligonucleotides to beads are described in, e.g., WO 2015/200541. In some embodiments, the oligonucleotide configured to link the hydrogel to the barcode is covalently linked to the hydrogel. Numerous methods for covalently linking an oligonucleotide to one or more hydrogel matrices are known in the art. As but one example, aldehyde derivatized agarose can be covalently linked to a 5'-amine group of a synthetic oligonucleotide. In some embodiments, the forward primers are linked to the bead or solid support via a cleavable linker (as described below) and can be cleaved from the bead or solid support in the partitions.

In some embodiments, a second oligonucleotide primer that functions as a reverse primer in combination with the first oligonucleotide primer on a target nucleic acid can be included in the partitions, or alternatively following combining of partitions into a bulk reaction. The target reverse primer, for example, will include a sequence that hybridizes to a reverse complement sequence on the target under the conditions of the assay to allow, for example, for polymerase-based extension. Thus for example, if a target sequence comprising a 5' sequence and a 3' sequence is present in a partition, the target reverse primer will have a 3' end identical to the 5' sequence of the target. This will allow hybridization of the 3' end of the target reverse primer to the extension product of the forward primer that uses the target nucleic acid as a template. Alternatively, the target reverse primer can initiate extension using the target nucleic acid as a template in which case that target reverse primer 3' sequence will be the reverse complement of the 5' sequence of the target nucleic acid. The target reverse primer can also have, for example, near or at its 5' end, a universal sequence (also referred to as a "PCR handle" or "adaptor" sequence).

Also included in the partitions is a partition ID tag oligonucleotide. This oligonucleotide comprises a variable partition ID tag sequence and a linking sequence (e.g., at the 3' end of the partition ID tag oligonucleotide) allowing the partition ID tag oligonucleotide to be linked to the forward primer. In some embodiments, the linking sequence is a reverse complement of all or a portion of (e.g., at least 6, 8, 10 12, 14, 16 or more nucleotides) the forward primer capture sequence or otherwise has a sequence to hybridize to the forward primer capture sequence. The variable partition ID tag sequence will differ between different partition ID tag oligonucleotides allowing the partition ID tag oligonucleotides to be distinguished from each other (and thus to distinguish between partitions). In some embodiments, the variable partition ID tag sequence is a sequence of about 6 to about 20 nucleotides, e.g., about 6-16, about 6-14, about 8-20, about 8-18, about 10-20, about 10-18, or about 12-20 nucleotides. The variable partition ID tag sequence can be random or designated, but will vary between partition ID tag oligonucleotides in different partitions.

In some embodiments, multiple copies of the same partition ID tag oligonucleotide are provided in a partition. This can be achieved, for example, when multiple copies of the partition ID tag oligonucleotides are linked to each other or to a common support that is delivered to the partition (optionally followed by release of individual copies from each other within the partition).

In other embodiments (e.g., when the partition ID tag oligonucleotides are not linked to each other), multiple copies of partition ID tags are introduced to each partition, but the copies in a particular partition do not necessarily share the same partition ID tag sequence. In these embodiments, the partition ID tag oligonucleotides have the same structure, but different partition ID tag sequences. If the length of the random partition ID tag sequences is long enough, the partition ID tag oligonucleotides can be added as a reagent at a concentration such that 10s, 100s or 1000s of different tag sequences populate each partition, but the likelihood of a specific tag sequence, or a specific set of partition ID tags, populating two separate partitions will be near zero. In these embodiments, the later association of forward primers from different beads with the same partition ID tag sequence (e.g., above the statistical level expected to occur randomly) will indicate the two beads were present in the same partition. In the case where unique sets of partition ID tags are in different partitions, statistical analyses (for example histogram comparison) can be used to distinguish partition ID tags from the same or different partitions.

The reverse complement of the forward primer capture sequence can be a reverse complement of the entire capture sequence of the forward primer or can be a reverse complement of a portion of the capture sequence so long as the forward primer capture sequence and the reverse complement sequence in the partition ID tag oligonucleotide can specifically hybridize in the subsequent reaction. In other embodiments, the linking sequence is complementary to a separate bridge single-strand nucleic acid sequence in the partition, allowing the linking sequence and the capture sequence of the forward primer to be brought into proximity for ligation when the capture sequence and linking sequence are simultaneously hybridized to the bridge sequence. In some embodiments, the target reverse primer further comprises a universal (e.g., "PCR handle") or other additional sequence to assist with downstream manipulation or sequencing of the amplicon. For example, when Illumina-based sequencing is used the target reverse primer can have a 5' P5 or P7 sequence (optionally with the forward primer having the other of the two sequences).

Spacer sequences can be included in the partition ID tag oligonucleotides to orient later sequencing. For example, in some embodiments, a constant sequence is included between the variable partition ID tag sequence and the linking sequence. In some embodiments, a constant sequence can also be included 5' of the variable partition ID tag sequence. Constant sequences have a specific non-variable sequence and set length such that they can be identified in a nucleotide sequence and can thus indicate the position of an adjacent variable partition ID tag sequence. The length of the constant sequences can be as convenient for sequencing and unique sequence identification. In some embodiments, each constant sequence is between 10-150 nucleotides.

In some embodiments, the 5' end of the partition ID tag oligonucleotide includes a primer binding site allowing for amplification or other manipulation of amplicons comprising the partition ID tag oligonucleotide via hybridization to the primer binding site. In some embodiments, the partition ID tag oligonucleotide further comprises a universal or other additional sequence to assist with downstream manipulation or sequencing of the amplicon. For example, when Illumina-based sequencing is used, the partition ID tag oligonucleotide can have a 5' P5 or P7 sequence (optionally with the forward primer having the other of the two sequences).

The number of copies of the partition ID tag oligonucleotide in a particular partition need not be high. Indeed, depending on the embodiment, it can be desirable to use as few copies as possible as only a small number of sequence reads of nucleic acids encompassing the partition ID tag sequence is needed to assess the presence of multiple forward primers. Thus, in some embodiments, an average of 1-50000 (e.g., 1-20, 5-50, 10-500, 100-20000) partition ID tag oligonucleotide copies are added per partition. The number of copies is enough to get good confirmation of bead occupancy in each partition, but few enough to conserve the majority of sequencing space for assay samples.

The partition ID tag oligonucleotide can be added to partitions as free oligonucleotide, or linked to a solid support (either a solid support different from or the same as the solid support linked to the forward primer). As examples, various aspects are depicted in FIG. 2. In some embodiments, the partition ID tag oligonucleotide is delivered to the partition as a free oligonucleotide, i.e., it is not linked to a solid support. In such embodiments, the partition ID tag oligonucleotide can be single-stranded (see, e.g., FIG. 2) or partially (see, e.g., FIG. 7) or fully double-stranded. Exemplary partial double stranded options include providing two partition ID tag oligonucleotides that hybridize at the partition ID tag sequence, one of the partition ID tag oligonucleotides having a reverse complement of the partition ID tag sequence, or portion thereof, of the partition ID tag sequence of the other partition ID tag oligonucleotide. An example of this embodiment is depicted in FIGS. 2 and 7-9. In these embodiments, the partially double-stranded molecules have 3' overhangs that comprise the capture sequence or a reverse complement thereof, leaving the capture sequences available for hybridization or otherwise interact with the capture sequence of the forward primer. This is advantageous for example in a situation where there are not multiple rounds of capture and extension in an assay. The double-stranded version allows each strand (forward and reverse-complement of tag sequence) to combine with a different forward primer in the same capture/extension step.

Figure 10:
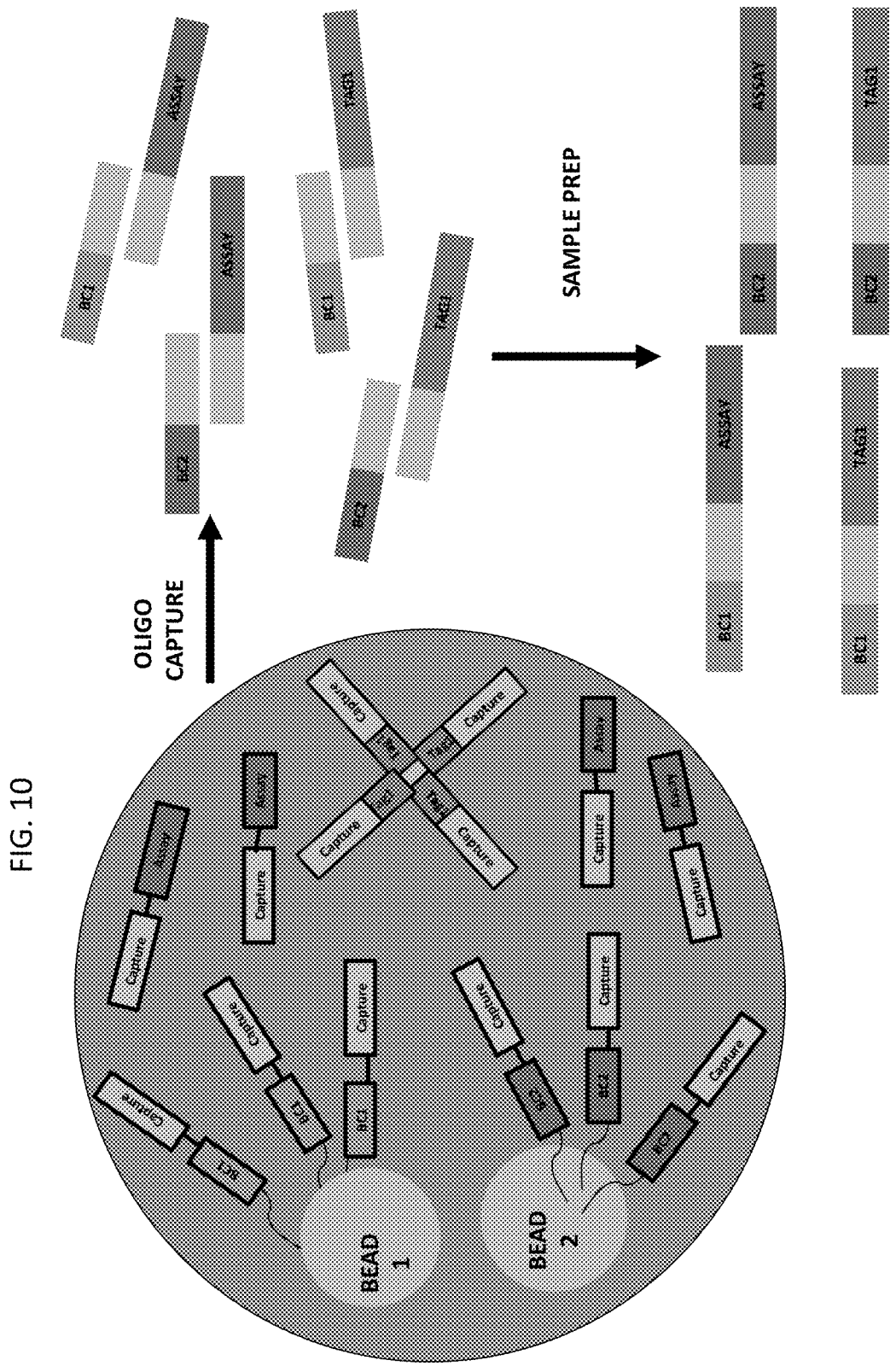
FIG. 10 depicts partition ID tags delivered attached to solid particles with multiple barcode beads.
Figure 11:
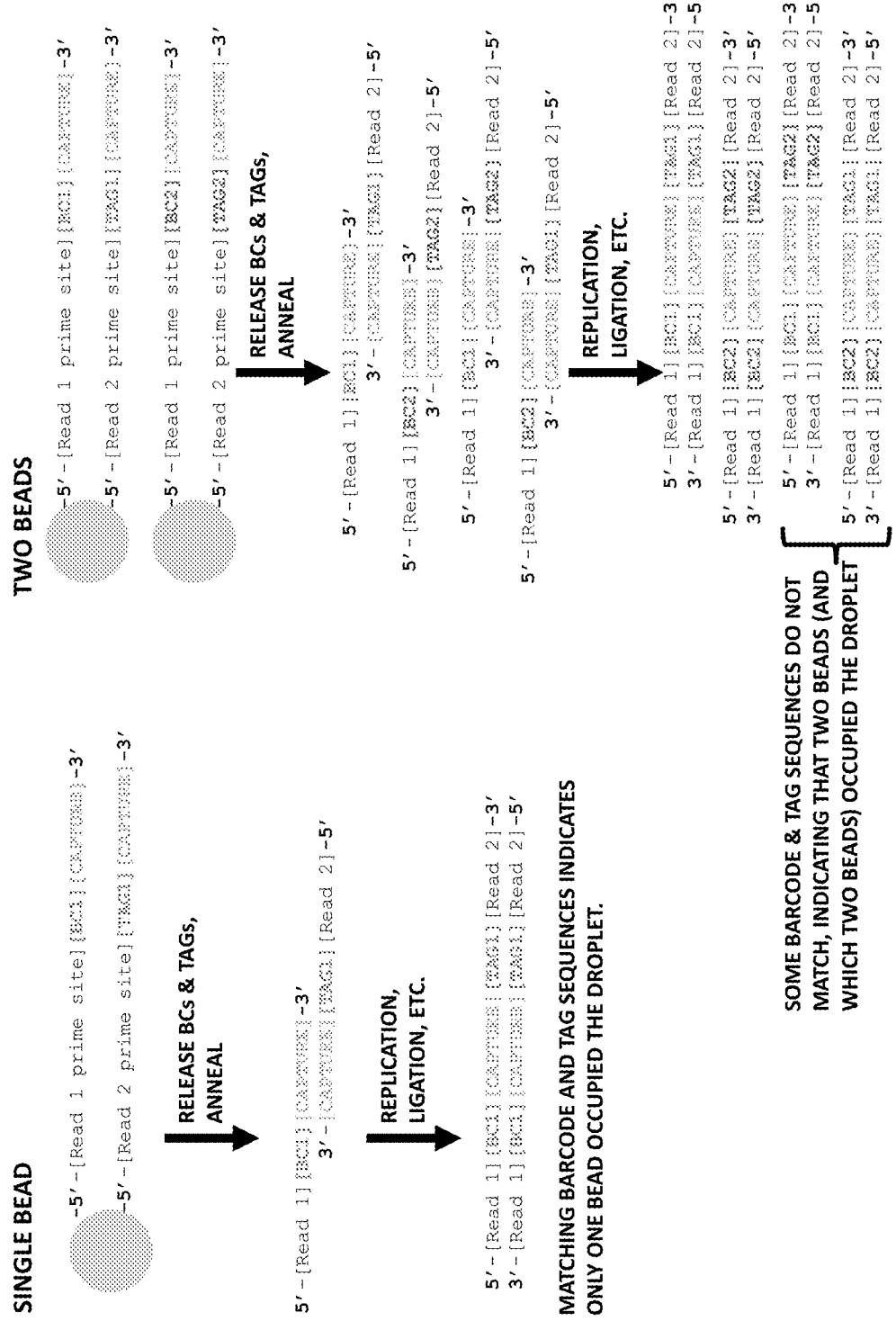
FIG. 11 depicts aspects in which the partition ID tags and barcoded forward primer are linked to the same bead. The "SINGLE BEAD" workflow shows the situation in which only one bead is in a partition. The "TWO BEADS" workflow shows the situation in which two beads are in a partition. In either aspect, the oligonucleotides are released from the beads in the partitions and then undergo replication. In the latter case, the resulting products will contain sequencing reads where the tag sequence and barcode are mis-matched compared to the initial beads, indicating that two beads were in the same partition.
Figure 12:
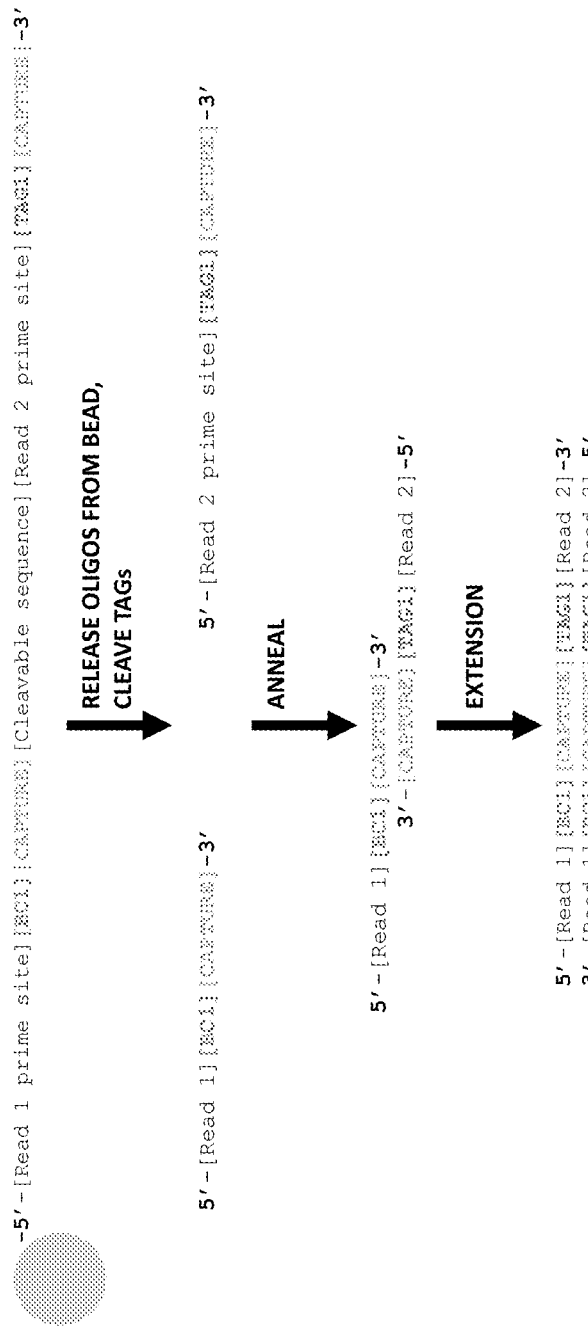
FIG. 12 depicts partition ID tags and barcodes built on the same beads and also as part of a single cleavable molecule. In the depicted aspect, the partition ID tag and the barcoded forward primer sequence are part of one oligonucleotide (which can be present in multiple copies) separated by a cleavable sequence, allowing for subsequent separation of the partition ID tag and forward primer in the partition. The workflow otherwise continues as described elsewhere herein.

In some embodiments, the single-stranded or double-stranded partition ID tag oligonucleotides are linked to a solid support when delivered to the partitions. See, e.g., FIG. 10-12. For example the partition ID tag oligonucleotides can be linked to a bead in some embodiments. In some embodiments, the partition ID tag oligonucleotides are linked to a separate solid support (e.g., a separate bead) than the solid support linked to the forward primers. Alternatively, the partition ID tag oligonucleotide can be delivered linked to the same solid support (e.g., bead) to which the forward primer is linked. In these embodiments, it can be desirable to include more forward primers on the solid support than partition ID tag oligonucleotides, for example limiting the number of partition ID tag oligonucleotides to the values indicated above for desirable numbers of partition ID tag oligonucleotides per partition. In either case, the number of beads delivered per partition can be adjusted so that a large number (e.g., at least a majority) of partitions contain one bead.

In some embodiments, once introduced into the partitions, partition ID tag oligonucleotides are cleaved from the solid support (e.g., bead) so that free partition ID tag oligonucleotides are more available to interact as described herein. Thus, in some embodiments, the partition ID tag oligonucleotides are linked to the solid support via a cleavable linker. In some cases, the tag reverse primer is attached to a solid support (e.g., bead) through a disulfide linkage (e.g., through a disulfide bond between a sulfide of the solid support and a sulfide covalently attached to the 5' or 3' end, or an intervening nucleic acid, of the oligonucleotide). In such cases, the oligonucleotide can be cleaved from the solid support by contacting the solid support with a reducing agent such as a thiol or phosphine reagent, including but not limited to a beta mercaptoethanol, dithiothreitol (DTT), or tris(2-carboxyethyl)phosphine (TCEP). In some embodiments, the cleavable linker is a restriction enzyme site that is cleaved by a restriction enzyme (e.g., an endonuclease such as a Type II endonuclease or Type IIS endonuclease). For example, in some embodiments, the cleavable linker comprises a Type II restriction enzyme binding site (e.g., HhaI, HindIII, NotI, BbvCI, EcoRI, BglI) or a Type IIS restriction enzyme binding site (e.g., FokI, AlwI, BspMI, MnlI, BbvI, BccI, MboI). In some embodiments, the cleavable linker comprises a uridine incorporated site in a portion of a nucleotide sequence. A uridine incorporated site can be cleaved, for example, using a uracil glycosylase enzyme (e.g., a uracil N-glycosylase enzyme or uracil DNA glycosylase enzyme). In some embodiments, the cleavable linker comprises a photocleavable nucleotide. Photocleavable nucleotides include, for example, photocleavable fluorescent nucleotides and photocleavable biotinylated nucleotides. See, e.g., Li et al., *PNAS*, 2003, 100:414-419; Luo et al., *Methods Enzymol*, 2014, 549:115-131.

In some embodiments, the partition ID tag oligonucleotide and the forward reverse primer are linked to each other via a cleavable linker (e.g., as described above) and are also linked to the solid support (e.g., bead). In this embodiment, the cleaving agent separates the forward primer and the partition ID tag oligonucleotide from each other and the solid support in the partition.

In yet further embodiments, one or more partition ID tag oligonucleotide can be linked (optionally via a cleavable linker as described above) to another molecule when delivered to a partition. As non-limiting examples, the partition ID tag oligonucleotide(s) can be linked to a protein (including but not limited to an antibody), biotin, polyethylene glycol (PEG), a gel (including but not limited to an agarose or acrylamide gel) or other molecule. In some embodiments, the molecule attached to the partition ID tag oligonucleotide is an affinity agent, i.e., an agent with affinity for other target molecules. Non-limiting examples of affinity agents include, e.g., antibodies and biotin.

In some embodiments, the partition ID tag oligonucleotide 3' end cannot be extended by a polymerase. For example, in some embodiments, the 3' end of the partition ID tag oligonucleotide is a dideoxy nucleotide (e.g., ddC). Blocking extension of the partition ID tag removes or reduces the possibility of subsequent preferential capture of the partition ID tag by the forward primer that initially captured it.

Following formation of the partitions containing the forward and reverse primers and the partition ID tag oligonucleotide, one can perform molecular methods for detection of a target nucleic acid in the partitions. Thus, in many embodiments, sample nucleic acids are also in the partition. Exemplary molecular methods can include any molecular method for detecting nucleic acids, including but not limited to, template-based primer extension (e.g., polymerase chain reaction) or methods that detect specific hybridization to a target nucleic acid via the forward primer capture sequence. In some embodiments, the method comprises ligation. Any of these molecular methods can be performed while the partitions are intact, or after the contents of the partitions have been merged (such that the methods are performed "in bulk"). In either option, in the partition, ID tag oligonucleotides are allowed to hybridize to at forward primers to form a hybridized product. The hybridized product can then be extended or otherwise amplified either within the partitions, or in bulk. As explained above, in addition to linkage (and optionally amplification) of the forward primer to a target nucleic acid, if present, the reaction will also link available copies of the partition ID tag oligonucleotide to some copies of the forward primers in the partition, thereby forming polynucleotides comprising a forward primer including the forward primer barcode sequence in the partition with the partition ID tag.

In some embodiments, the extension and/or amplification reaction comprises the use of a polymerase, e.g., a DNA polymerase. DNA polymerases for use in the methods described herein can be any polymerase capable of replicating a DNA molecule. In some embodiments, the DNA polymerase is a thermostable polymerase. Thermostable polymerases are isolated from a wide variety of thermophilic bacteria, such as *Thermus aquaticus* (Taq), *Pyrococcus furiosus* (Pfu), *Pyrococcus* woesei (Pwo), *Bacillus* sterothermophilus (Bst), *Sulfolobus acidocaldarius* (Sac) *Sulfolobus solfataricus* (Sso), Pyrodictium occultum (Poc), Pyrodictium *abyssi* (Pab), and *Methanobacterium* thermoautotrophicum (Mth), as well as other species. DNA polymerases are known in the art and are commercially available. In some embodiments, the DNA polymerase is Taq, Tbr, Tfl, Tru, Tth, Tli, Tac, Tne, Tma, Tih, Tfi, Pfu, Pwo, Kod, Bst, Sac, Sso, Poc, Pab, Mth, Pho, ES4, VENT™, DEEPVENT™, or an active mutant, variant, or derivative thereof. In some embodiments, the polymerase is Taq DNA polymerase. In some embodiments, the polymerase is a high fidelity DNA polymerase (e.g., iProof™ High-Fidelity DNA Polymerase, Phusion® High-Fidelity DNA polymerase, Q5® High-Fidelity DNA polymerase, Platinum® Taq High Fidelity DNA polymerase, Accura® High-Fidelity Polymerase). In some embodiments, the polymerase is a fast-start polymerase (e.g., FastStart™ Taq DNA polymerase or FastStart™ High Fidelity DNA polymerase). In some embodiments, the polymerase is a strand displacing polymerase (e.g., phi29, or Bst DNA Polymerase, Large Fragment).

In some embodiments, linking of the forward primer to the partition ID tag oligonucleotide comprises ligating the forward primer to the partition ID tag oligonucleotide. In some embodiments, the partitions comprise a bridge single strand nucleic acid. The bridge single strand nucleic acid can function to bring the forward primer and the partition ID tag oligonucleotide in proximity for ligation to each other. For example, the bridge single strand nucleic acid can comprise from 3' to 5', the 3' sequence of the target nucleic acid and a reverse complement of the linking sequence (e.g., 5' binding sequence) of the partition ID tag oligonucleotide such that hybridization of a forward primer and the partition ID tag oligonucleotide brings the 3' end of the forward primer adjacent to the 5' end of the partition ID tag oligonucleotide and wherein the 3' end of the forward primer is ligated to the 5' end of the partition ID tag oligonucleotide. In some embodiments, the bridge single strand nucleic acid is between 10-100 nucleotides in length. In some embodiments, the ligation reaction comprises the use of a ligase, e.g., a DNA ligase. Exemplary ligases for use in the methods described herein include, but are not limited to, T4 DNA ligase and T4 RNA ligase. Nucleic acid ligation methods are described in the art; see, e.g., Li et al., *Anal Biochem*, 2006, 349:242-246; and Kuhn et al., *FEBS J.*, 2005, 212:5991-6000.

Following the molecular reactions in the partitions (e.g., amplification or other linkage of the forward primer to partition ID tag oligonucleotides in the partitions and optional amplification or other manipulation of target nucleic acids in the partitions), the contents of the partitions are released prior to the downstream application, e.g., to pool multiple partitions for a downstream application such as a sequencing reaction. Partition breaking can be accomplished by any of a number of methods, including but not limited to electrical methods and introduction of a destabilizing fluid. See, e.g., Zeng et al., *Anal Chem* 2011, 83:2083-2089. Methods of breaking partitions are also described, for example, in US 2013/0189700, incorporated by reference herein.

In some embodiments, partitions are broken by mixing the partitions (e.g., droplets) with a destabilizing fluid. In some embodiments, the destabilizing fluid is chloroform. In some embodiments, the destabilizing fluid comprises a perfluorinated alcohol. In some embodiments, the destabilizing fluid comprises a fluorinated oil, such as a perfluorocarbon oil.

In some embodiments, the method further comprises purifying a target nucleic acid that is released from a partition (e.g., a target nucleic acid associated with a particle as described herein), e.g., in order to separate the target nucleic acid from other partition components. In some embodiments, the purifying step comprises the use of column-based purification methods (Zymo Select-a-Size Clean & Concentrator) or solid-phase reversible immobilization (SPRI) paramagnetic bead reagents. SPRI paramagnetic bead reagents are commercially available, for example in the Agencourt AMPure XP PCR purification system (Beckman-Coulter, Brea, Calif.).

In some embodiments, a nucleic acid from a partition as described herein is analyzed by a sequencing or genotyping method. In some embodiments, the nucleic acid is analyzed by sequencing, e.g., high throughput sequencing. In some embodiments, nucleic acids comprising the forward primer sequence (including the forward primer barcode) and the partition ID tag oligonucleotide (including the tag sequence) are sequenced. When multiple forward primer barcodes are associated with the same tag sequence, one can then assume that those multiple forward primers were within the same partition. When deconvoluting sequencing information from the partitions, the user can then use this information to improve sequencing results. For example, the user can exclude data from partitions where more than one forward primer was present from the sequencing data of remaining partitions. Alternatively, the user can use information from only one forward primer from a partition where multiple forward primers were present in the partition. Or sequencing information from all forward primers in one partition can be compiled and treated as if from a single partition.

Methods for high throughput sequencing and genotyping are known in the art. For example, such sequencing technologies include, but are not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety.

Exemplary DNA sequencing techniques include fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques understood in that art are utilized. In some embodiments, the present technology provides parallel sequencing of partitioned amplicons (PCT Publication No. WO 2006/0841,32, herein incorporated by reference in its entirety). In some embodiments, DNA sequencing is achieved by parallel oligonucleotide extension (See, e.g., U.S. Pat. Nos. 5,750,341; and 6,306,597, both of which are herein incorporated by reference in their entireties). Additional examples of sequencing techniques include the Church polony technology (Mitra et al., 2003, Analytical Biochemistry 320, 55-65; Shendure et al., 2005 Science 309, 1728-1732; and U.S. Pat. Nos. 6,432,360; 6,485,944; 6,511,803; herein incorporated by reference in their entireties), the 454 picotiter pyrosequencing technology (Margulies et al., 2005 Nature 437, 376-380; U.S. Publication No. 2005/0130173; herein incorporated by reference in their entireties), the Solexa single base addition technology (Bennett et al., 2005, Pharmacogenomics, 6, 373-382; U.S. Pat. Nos. 6,787,308; and 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 2000/018957; herein incorporated by reference in its entirety).

Typically, high throughput sequencing methods share the common feature of massively parallel, high-throughput strategies, with the goal of lower costs in comparison to older sequencing methods (See, e.g., Voelkerding et al., Clinical Chem., 55: 641-658, 2009; MacLean et al., Nature Rev. Microbiol., 7:287-296; each herein incorporated by reference in their entirety). Such methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and platforms commercialized by VisiGen, Oxford Nanopore Technologies Ltd., Life Technologies/Ion Torrent, and Pacific Biosciences, respectively.

In pyrosequencing (Voelkerding et al., Clinical Chem., 55: 641-658, 2009; MacLean et al., Nature Rev. Microbial., 7:287-296; U.S. Pat. Nos. 6,210,891; and 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotiter plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55. 641-658, 2009; MacLean et al., Nature Rev. Microbial., 7:287-296; U.S. Pat. Nos. 6,833,246; 7,115,400; and 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbial., 7:287-296; U.S. Pat. Nos. 5,912,148; and 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In some embodiments, nanopore sequencing is employed (See, e.g., Astier et al., J. Am. Chem. Soc. 2006 Feb. 8; 128(5)1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In some embodiments, HeliScope by Helicos BioSciences is employed (Voelkerding et al., Clinical Chem., 55. 641-658, 2009; MacLean et al., Nature Rev. Microbial, 7:287-

296; U.S. Pat. Nos. 7,169,560; 7,282,337; 7,482,120; 7,501,245; 6,818,395; 6,911,345; and 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (See, e.g., Science 327 (5970): 1190 (2010); U.S. Pat. Appl. Pub. Nos. 2009/0026082; 2009/0127589; 2010/0301398; 2010/0197507; 2010/0188073; and 2010/0137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers the hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

Another exemplary nucleic acid sequencing approach that may be adapted for use with the methods herein was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 2009/0035777, which is incorporated herein in its entirety.

Other single molecule sequencing methods include real-time sequencing by synthesis using a VisiGen platform (Voelkerding et al., Clinical Chem., 55: 641-58, 2009; U.S. Pat. No. 7,329,492; and U.S. patent application Ser. Nos. 11/671,956; and 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Another real-time single molecule sequencing system developed by Pacific Biosciences (Voelkerding et al., Clinical Chem., 55. 641-658, 2009; MacLean et al., Nature Rev. Microbiol., 7:287-296; U.S. Pat. Nos. 7,170,050; 7,302,146; 7,313,308; and 7,476,503; all of which are herein incorporated by reference) utilizes reaction wells 50-100 nm in diameter and encompassing a reaction volume of approximately 20 zeptoliters ($10^{-21}$ L). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In some embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters ($10^{-21}$ L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high concentrations, the detection volume is occupied by nucleotides only a small fraction of the time. In addition, visits to the detection volume are fast, lasting only a few microseconds, due to the very small distance that diffusion has to carry the nucleotides. The result is a very low background.

Processes and systems for such real time sequencing that may be adapted for use with the invention are described in, for example, U.S. Pat. Nos. 7,405,281; 7,315,019; 7,313,308; 7,302,146; and 7,170,050; and U.S. Pat. Pub. Nos. 2008/0212960; 2008/0206764; 2008/0199932; 2008/0199874; 2008/0176769; 2008/0176316; 2008/0176241; 2008/0165346; 2008/0160531; 2008/0157005; 2008/0153100; 2008/0153095; 2008/0152281; 2008/0152280; 2008/0145278; 2008/0128627; 2008/0108082; 2008/0095488; 2008/0080059; 2008/0050747; 2008/0032301; 2008/0030628; 2008/0009007; 2007/0238679; 2007/0231804; 2007/0206187; 2007/0196846; 2007/0188750; 2007/0161017; 2007/0141598; 2007/0134128; 2007/0128133; 2007/0077564; 2007/0072196; and 2007/0036511; and Korlach et al. (2008), "Selective aluminum passivation for targeted immobilization of single DNA polymerase molecules in zero-mode waveguide nanostructures," *PNAS* 105(4): 1176-81, all of which are herein incorporated by reference in their entireties.

In another aspect, partition libraries comprising a plurality of partitions (e.g., at least about 100; 200; 300; 500; 750; 1000; 2500; 5000; 7500; 10,000; 15,000; 20,000; 30,000, 40,000, 50,000, 70,000, 100,000, 150,000, 200,000, 300,000, 400,000, 500,000, 700,000, 1,000,000, or more partitions) are provided. In some embodiments, at least some partitions comprise (1) at least a forward primer, as described herein, optionally linked to a bead or other solid support, and (2) a partition ID tag oligonucleotide and optionally (3) a target reverse primer (which also may be added once the partitions have been combined in bulk, or optionally not included at all). In some embodiments, the partitions comprise 0, 1, or more than 1 particles per partition. In some embodiments, the partitions have an average of about one (e.g., 0.5-1.5) particle per partition. In some embodiments, the partitions have an average of about two (e.g., 1.5-2.5) particles per partition. In some embodiments, the partitions have an average of about three (e.g., 2.5-3.5) particles per partition. In some embodiments, the partition ID tag oligonucleotide is also linked to a solid support, which can be the same as or separate from the solid support linked to the forward primer. In some embodiments, the partitions comprise an amplicon comprising the forward primer and the partition ID tag oligonucleotide or complement thereof.

In some embodiments, at least some partitions of the partition library (e.g., a majority, substantially all, or all of the partitions of the partition library) further comprise a sample (e.g., one or more target nucleic acids, or one or more cells). In some embodiments, the sample comprising target nucleic acids comprises DNA, RNA, or a combination or hybrid thereof. In some embodiments, the sample is a sample comprising cells, e.g., is a single-cell sample. In some embodiments, the sample is a sample as described elsewhere herein.

In some embodiments, the partitions further comprise additional reagents or components for polymerization, amplification, reverse transcription, or primer extension (e.g., polymerases, salts, nucleotides, buffers, stabilizers, primers, detectable agents, or nuclease-free water) as described herein.

In another aspect, kits for generating a plurality of partitions as described herein are provided. In some embodiments, a kit comprises: (a) a plurality of beads comprising a solid support surface, the solid support surface having a plurality of forward primers conjugated thereon, wherein the forward primers comprise a barcode sequence and wherein at least a majority of the plurality of oligonucleotide primers conjugated to a solid support surface comprise the same barcode sequence; and (b) a partition ID tag oligonucleotide. In some embodiments, the kit further comprises (c) a target reverse primer. In some embodiments, the partition ID tag oligonucleotide is also linked to a solid support, which can be the same as or separate from the solid support linked to the forward primer.

In some embodiments, the kit further comprises one or more reagents for polymerization, amplification, reverse transcription, or primer extension (e.g., polymerases, salts, nucleotides, buffers, stabilizers, primers, detectable agents, or nuclease-free water) as described herein.

In some embodiments, the kit further comprises instructions for performing a method as described herein.

EXAMPLE

Figure 6:
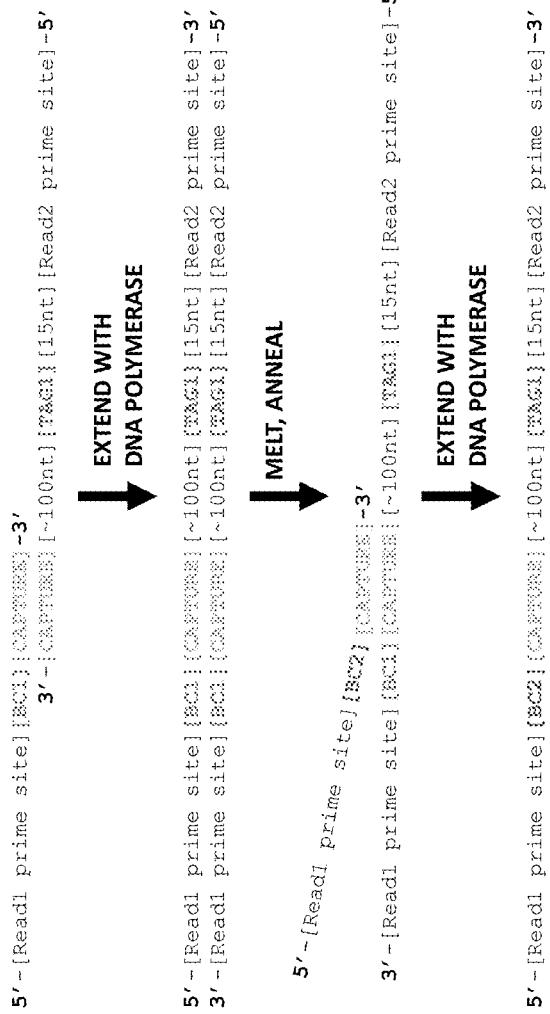
FIG. 6 depicts use of a single-stranded, in-solution partition ID tag without a chain terminator. The aspect depicted is similar to FIGS. 4-5, but in this case the partition ID tag itself can be extended. Nevertheless, because the BC1 and BC2 forward primers have the same capture regions, both the BC1 and BC2 amplicons will be generated that each contain TAG1.
Figure 7:
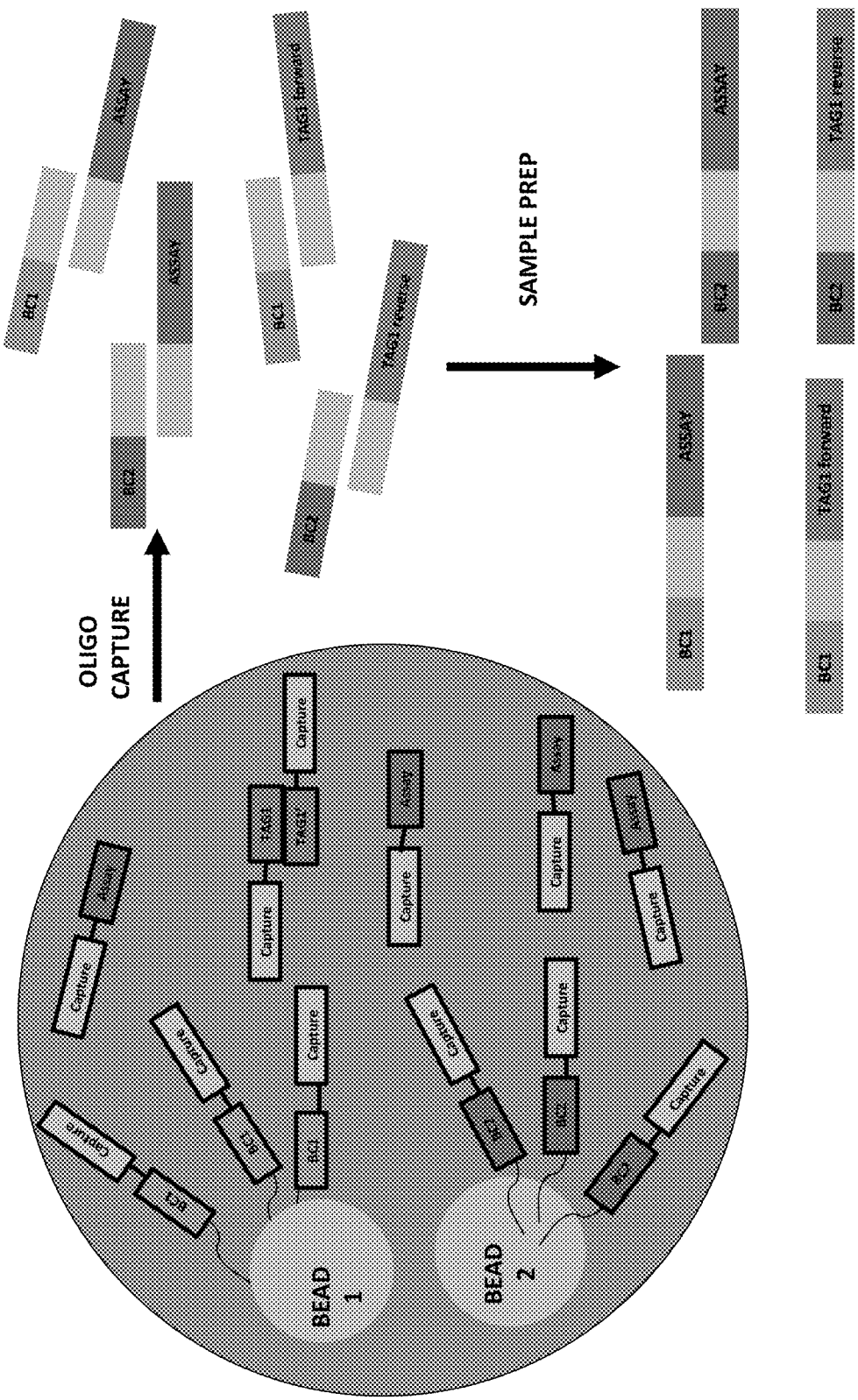
FIG. 7 depicts an aspect in which partially double-stranded partition ID tags are in solution with multiple barcode beads.
Figure 8:
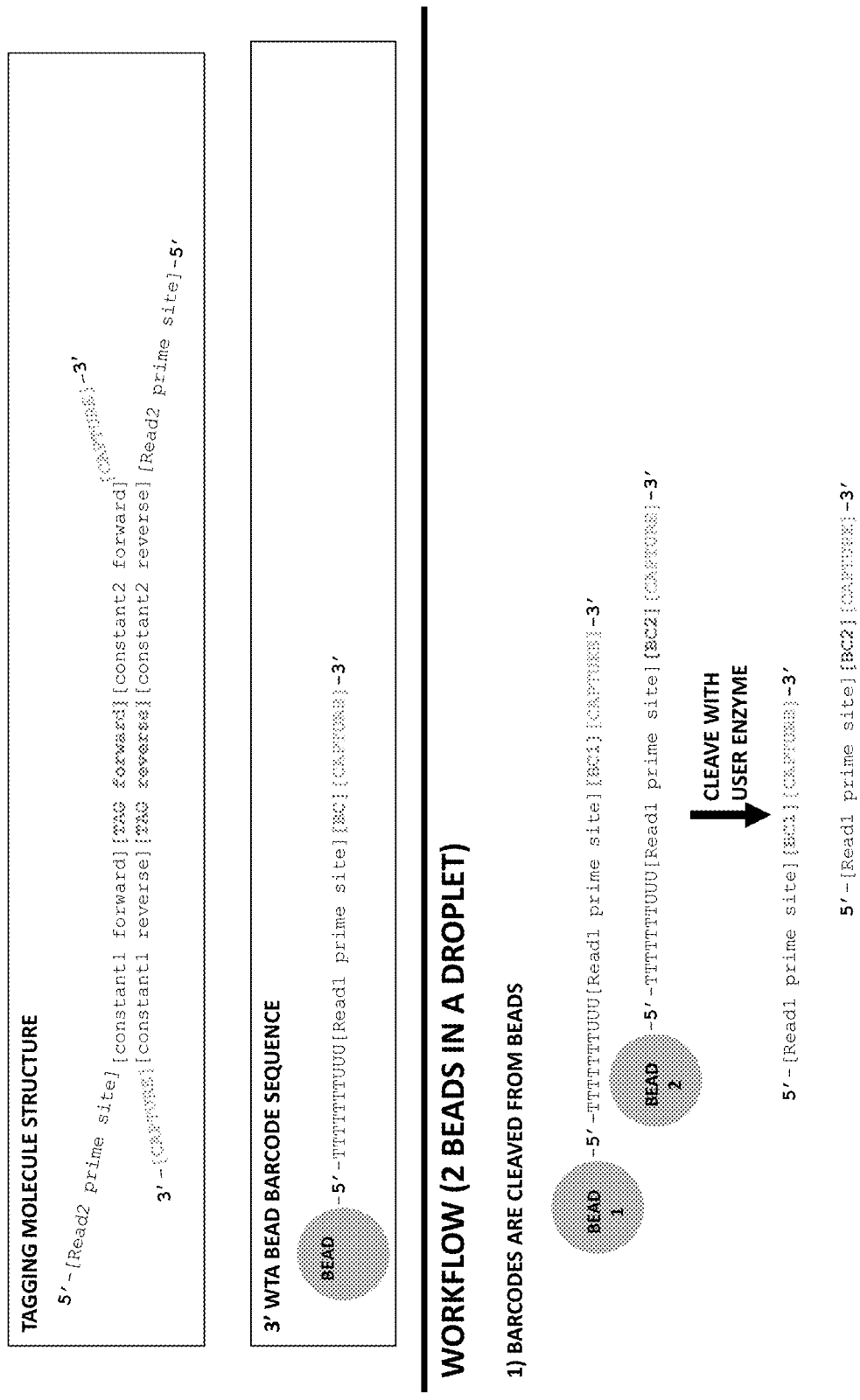
FIG. 8 depicts part 1 of a double-stranded partition ID tag example workflow. As shown, the partition ID tag is double-stranded at the tag sequence, and also in constant regions flanking the tag sequence. Separate 3' ends include single-stranded capture regions. The barcoded forward primer is depicted directly below the partition ID tag. The depicted workflow shows two beads having different barcodes (BC1 and BC2) in the same partition (as depicted a droplet). The forward primers linked to the beads are cleaved to release the barcoded forward primers. This workflow does not use multiple PCR steps, so forward and reverse tag sequences see different barcodes. There is a single oligonucleotide extension step occurring in the partition, not multiple cycles of melting, annealing, extending as in PCR. Each tagging molecule in this workflow involves combining a tag sequence to one bead's barcode, and the reverse-complement of that tag sequence to a second bead's barcode during the extension step. This is further addressed in the following description of FIG. 9.

Data from an experiment based on the disclosure of FIG. 6 is provided in the table depicted in FIG. 13. Barcodes were delivered to partitions on beads at ~$10^8$ per bead. Target DNA was tagmented single-cell nuclear DNA. Partition ID tags were delivered to partitions at levels of 0, 10, 100 or 1000 unique partition ID tags per partition. Barcodes were cleaved from their respective beads, allowed to capture target molecules and partition ID tags, and barcode/target and barcode/partition ID tag combined molecules were amplified for sequencing.

The table in FIG. 13 represents bioinformatics data from sequencing samples with the varying partition ID tag concentrations. As expected, the relative number of sequencing reads used for barcode/partition ID tag molecules vs. barcode/target molecules increased with increasing partition ID tag concentration (column 2).

Determination of "good" barcodes in the sequenced samples was performed using known methods, and the % of those "good" barcodes that were determined bioinformatically to be associated with at least 1 partition ID tag (column 3).

Two barcodes (X & Y) were determined to "overlap", or likely occupy the same partition, if they shared 2 or more common partition ID tags and if the number of sequencing reads of shared partition ID tags between X & Y is >10% of the smaller of the following two values: 1) # of total sequencing reads where partition ID tags associated with X, or 2) # of total sequencing reads where partition ID tags associated with Y. Column 4 shows the % of barcodes in each sample determined in this way not to overlap, and therefore to occupy a partition alone. In the system tested, the # of partition ID tags needed per partition to begin determining which barcodes share partitions with other barcodes is greater than 100 but may be less than 1000, as indicated by the inability to find a significant number of overlapping barcodes up to 100 partition ID tags per partition.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of detecting the presence or absence of multiple barcodes in a partition, the method comprising,
   forming partitions comprising
      forward primers comprising a barcode and a capture sequence complementary to a 3' sequence, or reverse complement thereof, of a sample target nucleic acid, wherein different partitions contain different forward primers comprising different barcode sequences unique to the partitions where the barcodes reside compared to barcodes present in other partitions and wherein in at least one partition the forward primers comprise copies of first and second forward primers comprising different barcode sequences,
      the sample target nucleic acid,
      multiple copies of a partition ID tag oligonucleotide having a combination of sequences unique to the partition in which the partition ID tag oligonucleotide resides and_comprising a 3' end sequence that comprises a reverse complement of the capture sequence and a 5' sequence comprising a variable partition ID tag sequence, wherein the partition ID tag oligonucleotide is a DNA oligonucleotide;
   in the partitions, hybridizing the capture sequence of at least some copies of the first and the second forward primers to different copies of the partition ID tag oligonucleotide to form hybridized products, and hybridizing the capture sequence of other copies of the first and the second forward primers to the sample target nucleic acid;

performing polymerase chain reaction amplification on the hybridized products to form amplicons, wherein at least some amplicons are formed from a first forward primer and the partition ID tag oligonucleotide and at least some amplicons are formed from a second forward primer and the partition ID tag oligonucleotide; and sequencing the amplicons, wherein if different forward primers form amplicons with the same variable partition ID tag sequence in a partition, the different forward primers are from the same partition, wherein the partition ID tag oligonucleotide comprises a double-stranded variable partition ID tag sequence and one or two single-stranded 3' ends comprising the reverse complement of the capture sequence.

2. The method of claim 1, wherein the forward primers, the partition ID tag oligonucleotide, or both further comprise a universal adaptor sequence.

3. The method of claim 1, wherein the performing also amplifies the sample target nucleic acid with the forward primers and sample target reverse primers to form an amplification product and the sequencing comprises sequencing the amplification products.

4. The method of claim 1, wherein in the partition forming step the forward primers are linked to a bead.

5. The method of claim 4, wherein the forward primers are cleaved from the bead before the amplifying.

6. The method of claim 1, wherein multiple copies of partition ID tag oligonucleotides are linked to each other.

7. The method of claim 6, wherein the multiple copies are linked to each other through a bead.

8. The method of claim 7, wherein the bead is linked to forward primers and partition ID tag oligonucleotides and the bead comprises at least 10 times the number of the forward primers compared to the partition ID tag oligonucleotides linked to the bead.

9. The method of claim 6, wherein during partition forming the forward primers and the partition ID tag oligonucleotides are linked to each other via a cleavable linker and the method further comprises cleaving the cleavable linker before the amplification.

10. The method of claim 1, wherein the partition ID tag oligonucleotide is single-stranded.

11. The method of claim 1, wherein the variable partition ID tag sequence is double-stranded and comprises two single-stranded 3' ends comprising the reverse complement of the capture sequence.

12. The method of claim 1, wherein during the partition forming step the partition ID tag oligonucleotide is linked to a solid support.

13. The method of claim 1, wherein the partition ID tag oligonucleotide comprises an affinity tag.

14. The method of claim 13, wherein the affinity tag is biotin, an antibody, or an aptamer.

15. The method of claim 1, wherein the partitions are droplets.

16. The method of claim 1, wherein contents of the partitions comprising the hybridized product are combined before the amplifying.

17. The method of claim 1, wherein sample target reverse primers are present in the partitions.

18. The method of claim 1, wherein sample target reverse primers are introduced after contents of the partitions are combined.

19. The method of claim 1, wherein the amplification occurs while the hybridized products are within the partitions.

20. The method of claim 1, wherein the partition ID tag oligonucleotide is 4-50 nucleotides in length.

21. The method of claim 1, wherein the variable partition ID tag sequence is double-stranded and comprises only one single-stranded 3' end comprising the reverse complement of the capture sequence.

* * * * *